United States Patent [19]

Ishikawa

[11] Patent Number: 5,607,819
[45] Date of Patent: Mar. 4, 1997

[54] COLOR DEVELOPER AND PROCESSING METHOD USING THE SAME

[75] Inventor: Takatoshi Ishikawa, Minami-ashigara, Japan

[73] Assignee: Fuji Photo Film Co., Ltd., Kanagawa-ken, Japan

[21] Appl. No.: 321,863

[22] Filed: Oct. 14, 1994

Related U.S. Application Data

[63] Continuation of Ser. No. 73,476, Jun. 9, 1993, abandoned.

[30] Foreign Application Priority Data

Jun. 10, 1992 [JP] Japan ................... 4-175038

[51] Int. Cl.⁶ ................... G03C 7/30
[52] U.S. Cl. ................... 430/386; 430/387; 430/486; 430/487; 430/488
[58] Field of Search ................... 430/357, 386, 430/387, 434, 446, 486, 487, 488

[56] References Cited

U.S. PATENT DOCUMENTS

| | | |
|---|---|---|
| 3,725,067 | 3/1973 | Bailey et al. |
| 4,001,020 | 1/1977 | Hayashi et al. ................... 430/487 |
| 4,414,305 | 11/1983 | Nakamura et al. ................... 430/489 |
| 4,540,654 | 9/1985 | Sato et al. ................... 430/381 |
| 4,717,648 | 1/1988 | Ueda et al. ................... 430/487 |
| 4,774,169 | 9/1988 | Kuse et al. ................... 430/467 |
| 4,798,783 | 1/1989 | Ishikawa et al. ................... 430/372 |
| 4,920,043 | 4/1990 | Ohashi et al. ................... 430/611 |
| 5,217,857 | 6/1993 | Hayashi ................... 430/556 |
| 5,272,044 | 12/1993 | Nishigaki et al. ................... 430/393 |

FOREIGN PATENT DOCUMENTS

| | | |
|---|---|---|
| 0243168 | 10/1987 | European Pat. Off. |
| 0246624 | 11/1987 | European Pat. Off. |
| 0529526 | 3/1993 | European Pat. Off. |
| 59-114538 | 7/1984 | Japan. |
| 1935310 | 2/1970 | Netherlands. |

*Primary Examiner*—Hoa Van Le
*Attorney, Agent, or Firm*—Birch, Stewart, Kolasch & Birch, LLP

[57] ABSTRACT

There is disclosed a color developer and a method for processing a silver halide color photographic material using said color developer. The color developer comprises a thiourea compound represented by the formula (I):

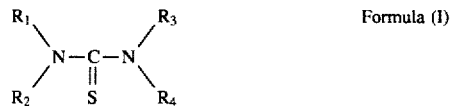

Formula (I)

wherein $R_1$, $R_2$, $R_3$, and $R_4$ each represent a hydrogen atom, a substituted or unsubstituted alkyl group, a substituted or unsubstituted aryl group, or a substituted or unsubstituted cycloalkylene group, provided that two or more of $R_1$, $R_2$, $R_3$, and $R_4$ each do not represent a hydrogen atom at the same time; at least one pair of $R_1$ and $R_3$, and $R_2$ and $R_4$, together may bond to form a nitrogen-containing heterocyclic ring; or at least one pair of $R_1$ and $R_2$, and $R_3$ and $R_4$, together may bond to form a ring.

23 Claims, No Drawings

COLOR DEVELOPER AND PROCESSING METHOD USING THE SAME

This application is a continuation of application Ser. No. 08/073,476, filed on Jun. 9, 1993, now abandoned.

FIELD OF THE INVENTION

The present invention relates to a novel color developer and a method for processing a silver halide color photographic material using said color developer. More particularly the present invention relates to a color developer and a processing method wherein fluctuation of photographic properties (particularly the processing speed and the image-gradation) with continuous processing and with the contamination by fixing components is made small.

BACKGROUND OF THE INVENTION

In the method for processing a silver halide color photographic material, the most stable and preferable continuous processing is that which maintains the original photographic properties at all times during the processing. At continuous processing, the processing is generally carried out while constantly replenishing a replenisher in a certain amount per unit area of the photographic material to be processed. However, the preciseness of replenishing pumps being used in the replenishment is not perfect, and it is often observed that over-replenishment or under-replenishment is made, causing fluctuation of photographic properties.

Also, at continuous processing, sometimes contamination by undesired other processing solution happens occurs. In particular, when a color developer is contaminated with a solution having a fixing function (e.g., a bleach-fix solution or a fixing solution), since the silver halide in the photographic material is dissolved, photographic properties are changed considerably, sometimes making the production impossible. In many cases such contamination takes place when the solution is prepared or when the apparatus has a problem.

On the other hand, in comparison with conventionally used pyrazolone magenta couplers, pyrazoloazole magenta couplers, such as pyrazolotriazoles, have the advantage that the hue and the image preservability are excellent. For example, pyrazoloazole couplers are described in U.S. Pat. Nos. 4,540,654 and 3,725,067. They are, however, relatively susceptible to the above fluctuation of processing, and a technique to solve this problem is desirably sought.

Thione compounds represented by formula (I) of the present invention are described in JP-A ("JP-A" means unexamined published Japanese patent application) No. 114538/1984 and are used in the DTR (diffusion transfer reversal), development process, which is intended to obtain high sensitivity, high contrast, and high sharpness. On the other hand, the present invention relates to a conventional color image forming system that comprises processing a photographic material comprising a negative emulsion with a color developer comprising a p-phenylenediamine developing agent, followed by desilvering. The present invention uses a p-phenylenediamine developing agent in a color developer in order to improve the stability with continuous processing, and since it is used in a system different from the former and its effect is different, the present invention cannot be inferred from said reference.

Although U.S. Pat. No. 4,920,043 discloses a technique that uses special thiols or thiones as antifoggants, it is a technique for preventing fogging of black and white development. The document does not refer to the stabilization in color development at the time of continuous processing at all, and thus the present invention cannot be inferred from the description of the document.

SUMMARY OF THE INVENTION

Therefore, an object of the present invention is to provide a color developer that does not induce fluctuations of photographic properties caused by over or under of replenishing amounts and due to the contamination by fixing agent or the like, during the continuous processing of silver halide color photographic material.

Another object of the present invention is to provide a method for processing a silver halide color photographic material that can obtain constant quality by stabilizing the fluctuation of photographic properties caused by over or under of the replenishing amount and the fluctuation of photographic properties due to contamination that occurs during continuous processing of a color photographic material.

Other and further objects, features, and advantages of the invention will appear more evident from the following description.

DETAILED DESCRIPTION OF THE INVENTION

It has been found that the object of the present invention can be achieved by carrying out the following technique:

(1) A color developer comprising at least one thiourea compound represented by the following formula (I):

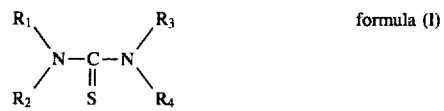

wherein $R_1$, $R_2$, $R_3$, and $R_4$ each represent a hydrogen atom, a substituted or unsubstituted alkyl group, a substituted or unsubstituted aryl group, or a substituted or unsubstituted cycloalkylene group, provided that two or more of $R_1$, $R_2$, $R_3$, and $R_4$ each do not represent a hydrogen atom at the same time; at least one pair of $R_1$ and $R_3$, and $R_2$ and $R_4$, together may bond to form a nitrogen-containing heterocyclic ring; or at least one pair of $R_1$ and $R_2$, and $R_3$ and $R_4$, together may bond to form a ring.

(2) A method for processing a silver halide color photographic material, which comprises processing said silver halide color photographic material with a color developer stated under (1).

(3) The method for processing a silver halide color photographic material stated under (2), wherein said silver halide color photographic material contains at least one pyrazoloazole magenta coupler.

(4) The method for processing a silver halide color photographic material stated under (3), wherein said pyrazoloazole magenta coupler is selected from magenta couplers represented by the following formula (M):

wherein $R_5$ represents a hydrogen atom or a substituent, Z represents a group of non-metallic atoms required to form a 5-membered azole ring containing 2 to 4 nitrogen atoms, which azole ring may contain a substituent (including a condensed ring), and X represents a group capable of being released upon coupling reaction with the oxidized product of a developing agent.

(5) The method for processing a silver halide color photographic material stated under (2), wherein said color developer contains thiosulfate radicals in an amount of $1 \times 10^{-4}$ mol/l or more.

In the present invention, when a pyrazoloazole magenta coupler, particularly a magenta coupler represented by formula (M), is used, a remarkable effect can be exhibited. Further, when the color developer is contaminated with a thiosulfate, the method using above magenta coupler is a very effective means capable of making its harmful influence null.

It is completely unexpected that the above-described thiourea compound is effective against problems of photographic properties, such as contamination, resulting from processing of a color photographic material that uses a pyrazoloazole magenta coupler.

Now the compound represented by formula (I) will be described.

In formula (I), $R_1$, $R_2$, $R_3$, and $R_4$, which may be the same or different, each represent a hydrogen atom or a substituted or unsubstituted alkyl group, aryl group, or cycloalkylene group, provided that two or more of $R_1$, $R_2$, $R_3$, and $R_4$ each do not represent a hydrogen atom at the same time.

The alkyl group is preferably an alkyl group having about 1 to 10 carbon atoms, particularly preferably 1 to 4 carbon atoms. As the aryl group, a phenyl group and a naphthalene group can be mentioned. The cycloalkylene group is preferably a cyclopropane group and a cyclohexyl group.

Further, the alkyl group, the aryl group, and the cycloalkylene group may have various substituents (e.g., a hydroxyl group, a carboxyl group, an alkoxy group, a sulfonic group, a phosphonic group, a halogen atom, an amino group, and a sulfonamido group).

$R_1$, $R_2$, $R_3$, and $R_4$ may be the same or different but two or more of $R_1$, $R_2$, $R_3$, and $R_4$ each do not represent a hydrogen atom at the same time. The compound having two or more hydrogen atoms causes the color density to lower conspicuously and therefore is not preferable in the system of the present invention.

At least one pair of $R_1$ and $R_3$, and $R_2$ and $R_4$ together may bond to form a nitrogen-containing heterocyclic ring, and particularly preferably to form a 5- or 6-membered ring. Alternatively, at least one pair of $R_1$ and $R_2$, and $R_3$ and $R_4$, together may bond to form a ring. The ring may be an aliphatic ring, an aromatic ring, or a heterocyclic ring, with particular preference given to a 6-membered ring.

Preferable compounds of the present invention are shown below, but the present invention is not restricted to them.

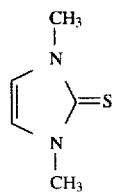

I-1

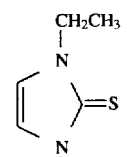

I-2

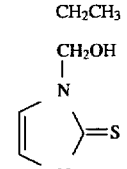

I-3

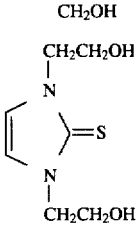

I-4

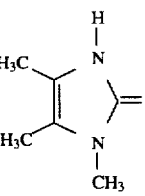

I-5

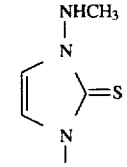

I-6

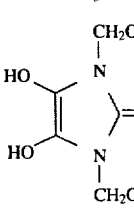

I-7

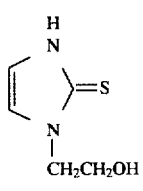

I-8

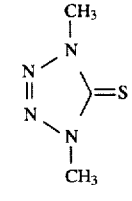

I-9

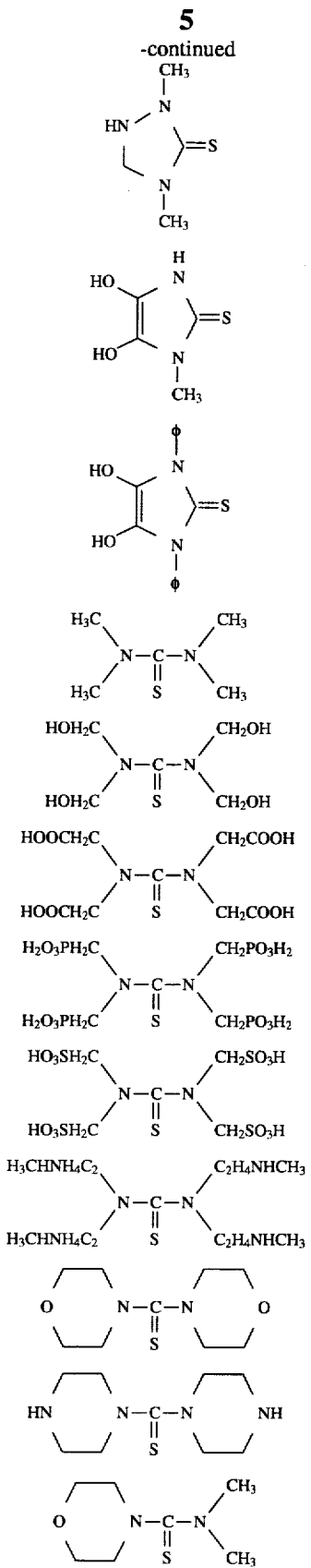

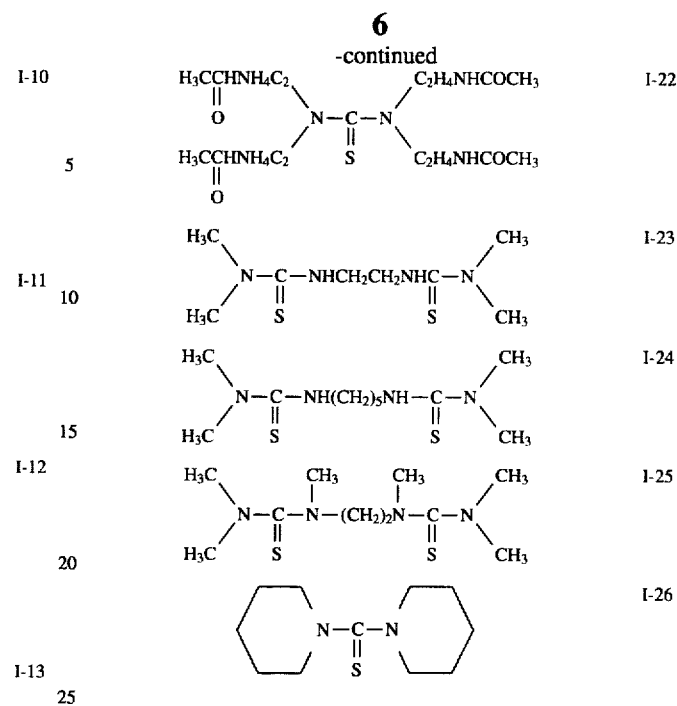

The compound represented by formula (I) can be synthesized, for example, by the commonly known ammonium rhodanide process, the diazomethane process, or the lime nitrogen process. Some of the compounds may be commercially available. Alternatively, the compound can be synthesized by a process described, for example, in JP-A No. 229449/1988 or U.S. Pat. No. 3,801,330.

The amount of these compounds to be added is about 0.001 to 10 g, preferably about 0.05 to 1.0 g, per liter of the color developer.

Now the coupler represented by formula (M) will be described in detail. Preferable skeletons among coupler skeletons represented by formula (M) are 1H-imidazo-[1,2-b]pyrazole, 1H-pyrazolo[1,5-b][1,2,4]triazole, 1H-pyrazolo [5,1-c][1,2,4]triazole, 1H-pyrazolo[1,5-d]tetrazole, and 1H-pyrazolo[1,5-a]benzimidazole.

Out of the pyrazoloazole couplers represented by formula [M], imidazo[1,2-b]pyrazoles described in U.S. Pat. No. 4,500,630, pyrazolo[1,5-b][1,2,4]triazoles described in U.S. Pat. No. 4,540,654, and pyrazolo[5,1-c][1,2,4]triazoles described in U.S. Patent No. 3,725,067 are preferable in view of the absorption properties of the color-formed dyes; and out of them, pyrazolo[1,5-b][1,2,4]triazoles are particularly preferable in view of the light fastness.

Details of substituents on the azole ring represented by the substituents $R_1$, X, and Z are described, for example, in U.S. Pat. No. 4,540,654, from the second column, line 41, to the eighth column, line 27. Preferable ones are pyrazoloazole couplers wherein a branched alkyl group is directly linked to the 2-, 3-, or 6-position of the pyrazolotriazole, as described in JP-A 65245/1986 and JP-B ("JP-B" means examined Japanese patent publication) No. 60167/1990; pyrazoloazole couplers containing a sulfonamido group in the molecule, as described in JP-A No. 65246/1986; pyrazoloazole couplers having an alkoxyphenylsulfonamido ballasting group, as described in JP-A No.147254/1986; pyrazolotriazole couplers having an alkoxy group or an aryloxy group in the 6-position, as described in JP-A Nos. 209457/1987 and 307453/1988; pyrazolotriazole couplers having a phenylene group in the 2-position, as described in JP-A No. 41851/ 1988; and pyrazolotriazole couplers having a carbonamido group in the molecule, as described in Japanese Patent Application No. 22279/1989.

Out of these couplers, specific examples of pyrazolotriazole couplers are listed below.

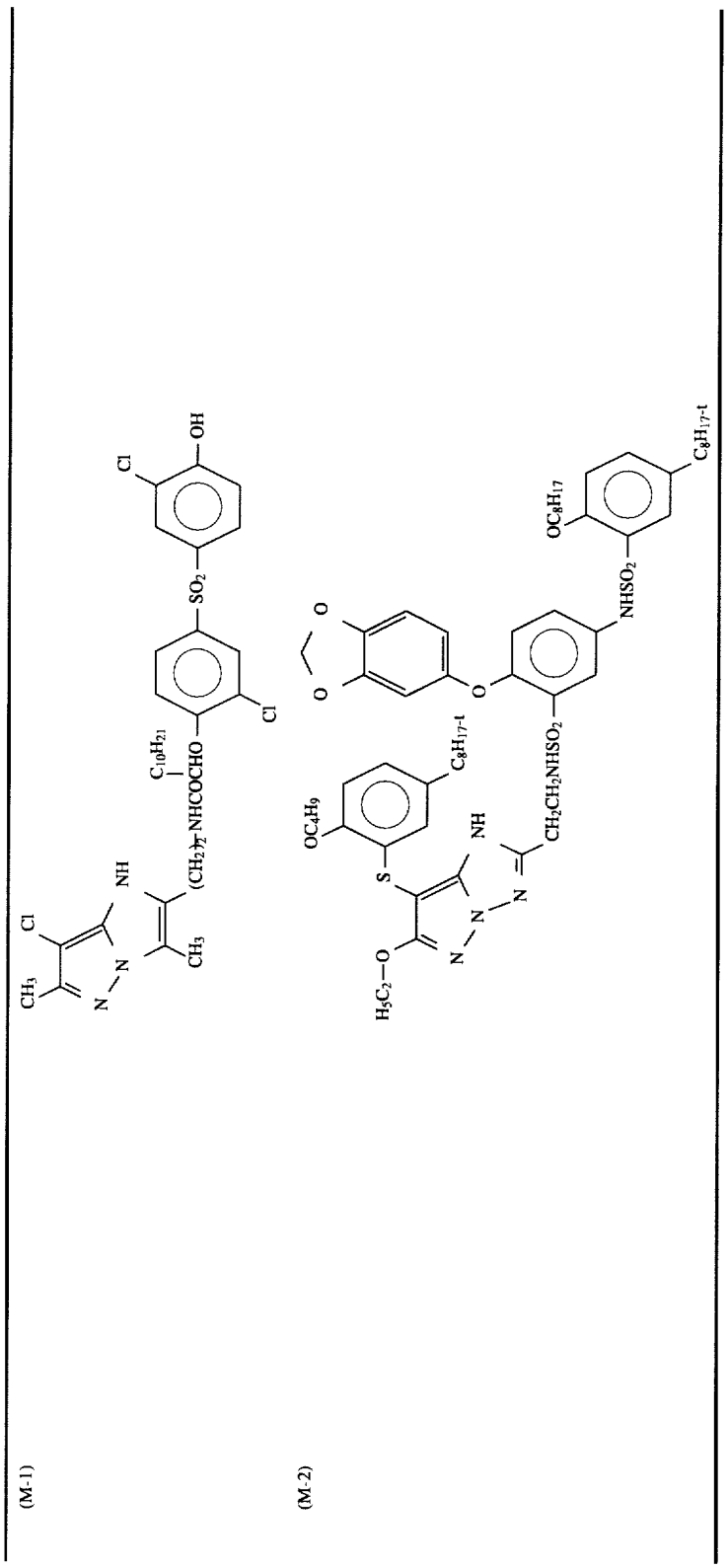

-continued

| Compound | R₁ | R₂ | X |
|---|---|---|---|
| M-3 | CH₃— | ![structure with -CHCH₂NHSO₂-CH₃ connected to phenyl with OC₈H₁₇(n), and phenyl with OC₈H₁₇(n) and C₈H₁₇(t) via NHSO₂] | Cl |
| M-4 | " | ![structure with -CHCH₂NHSO₂-CH₃ connected to phenyl with OCH₂CH₂OC₂H₅, and phenyl with OC₈H₁₇(n) and C₈H₁₇(t) via NHSO₂] | " |
| M-5 | " | ![structure with -CH-CH₃ connected to phenyl with OCH₂CH₂OC₆H₁₃(n) and C₈H₁₇(t)] | " |
| M-6 | " | ![structure with -CHCH₂NHCOCHO-CH₃ / C₆H₁₃(n), connected to phenyl with OC₅H₁₁(t) and C₅H₁₁(t)] | " |

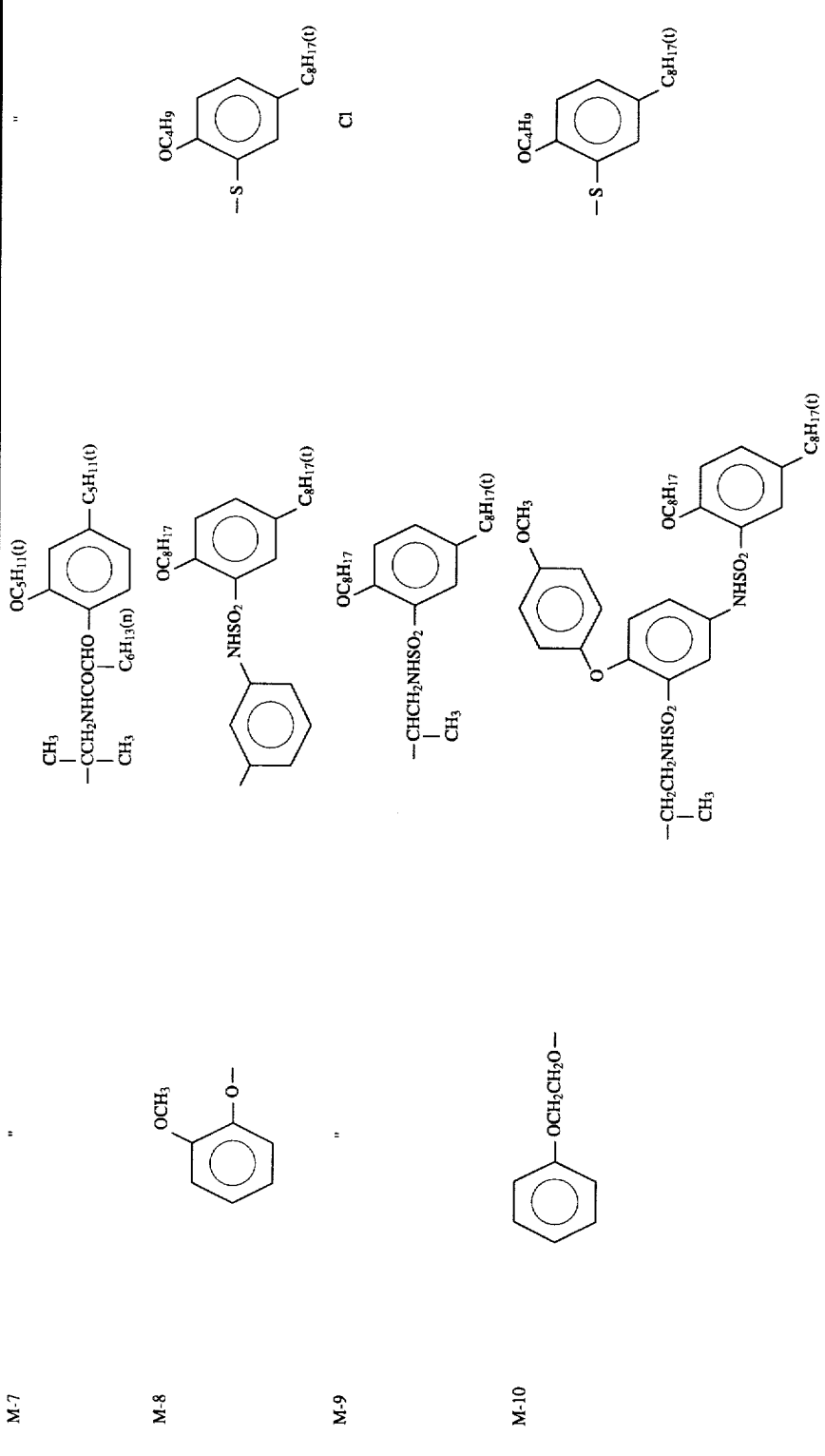

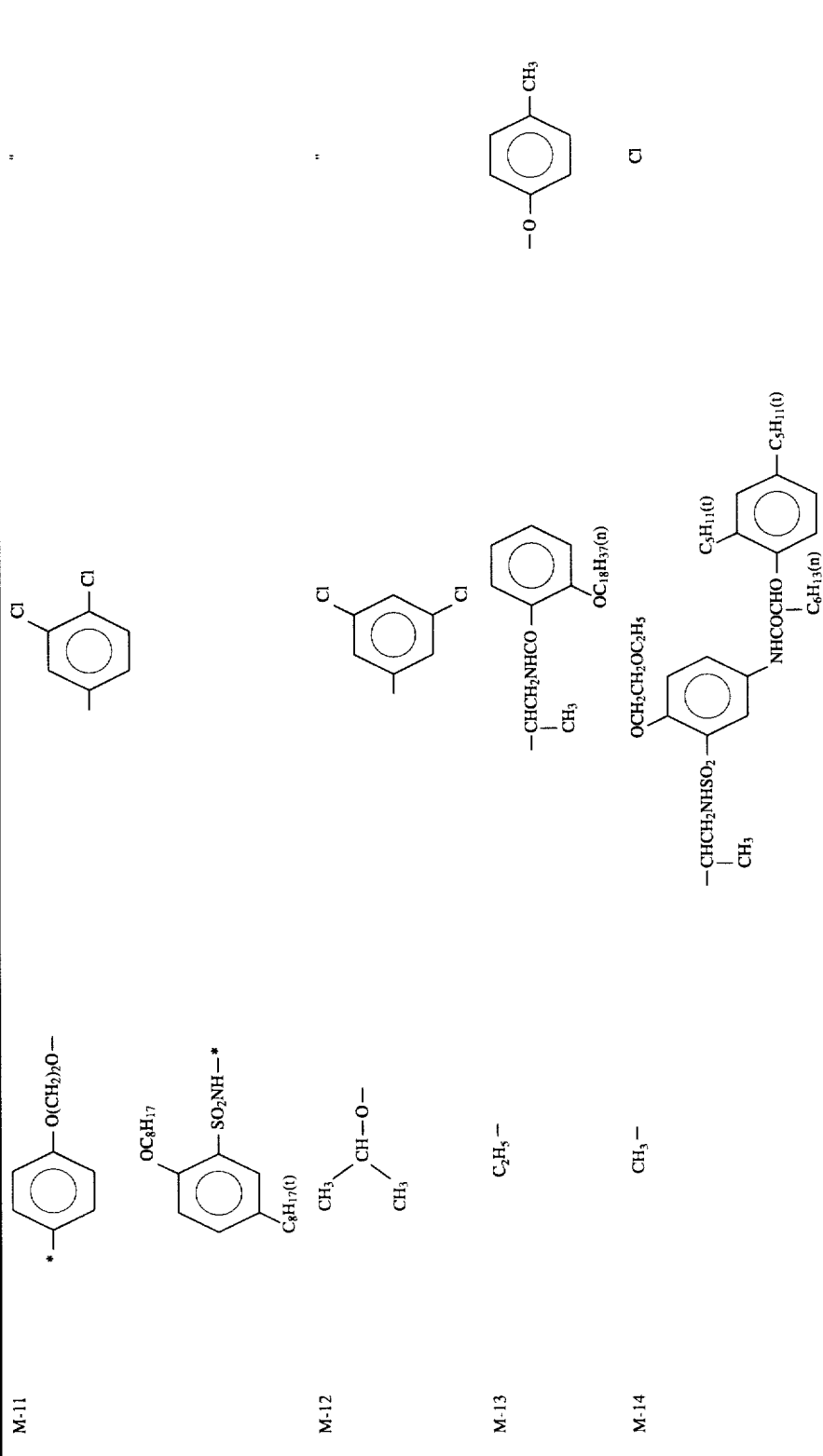

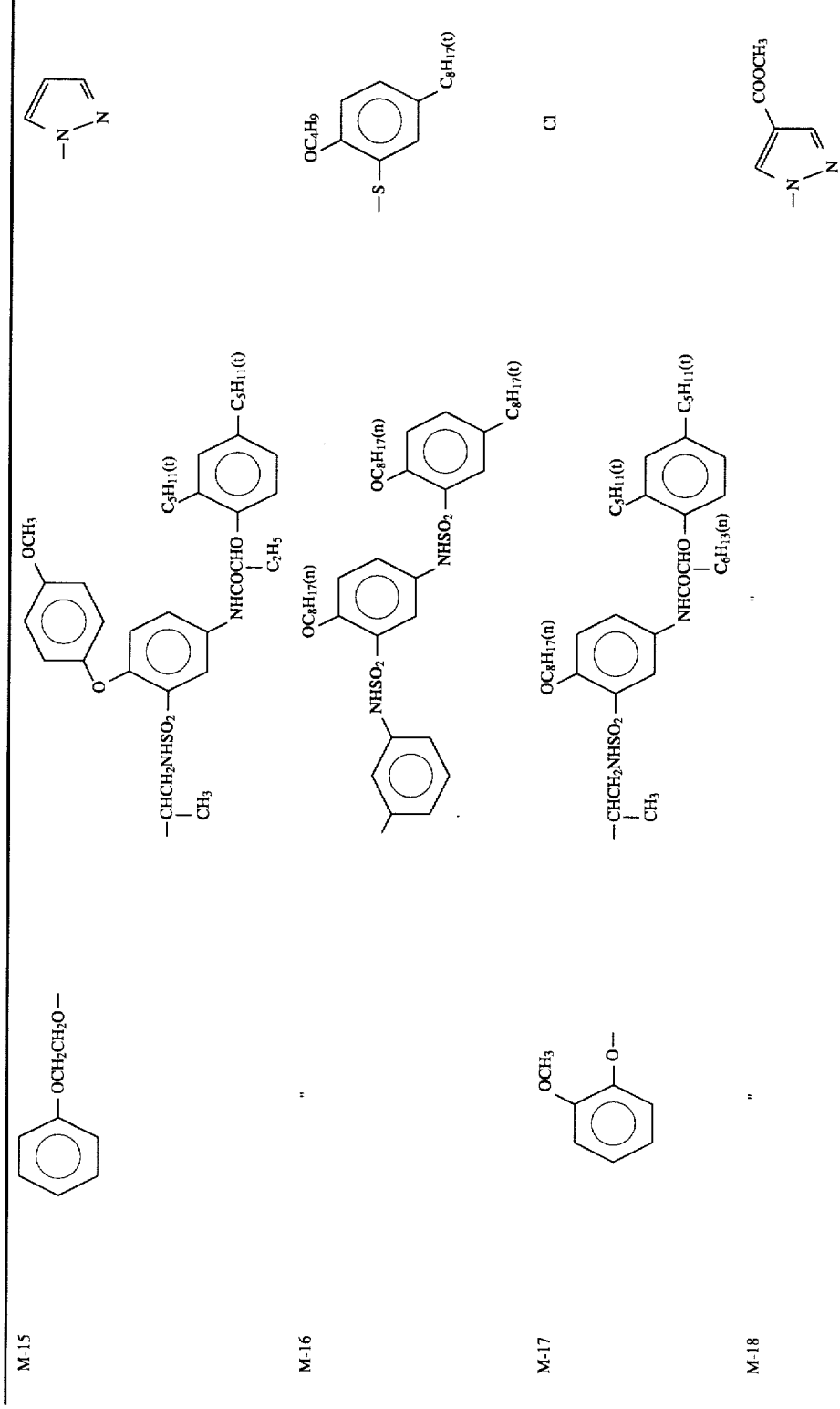

| Compound | $R_1$ | $R_2$ | X |
|---|---|---|---|
| M-22 | $CH_3-$ | (structures) | Cl |
| M-23 | " | | " |
| M-24 | " | | " |

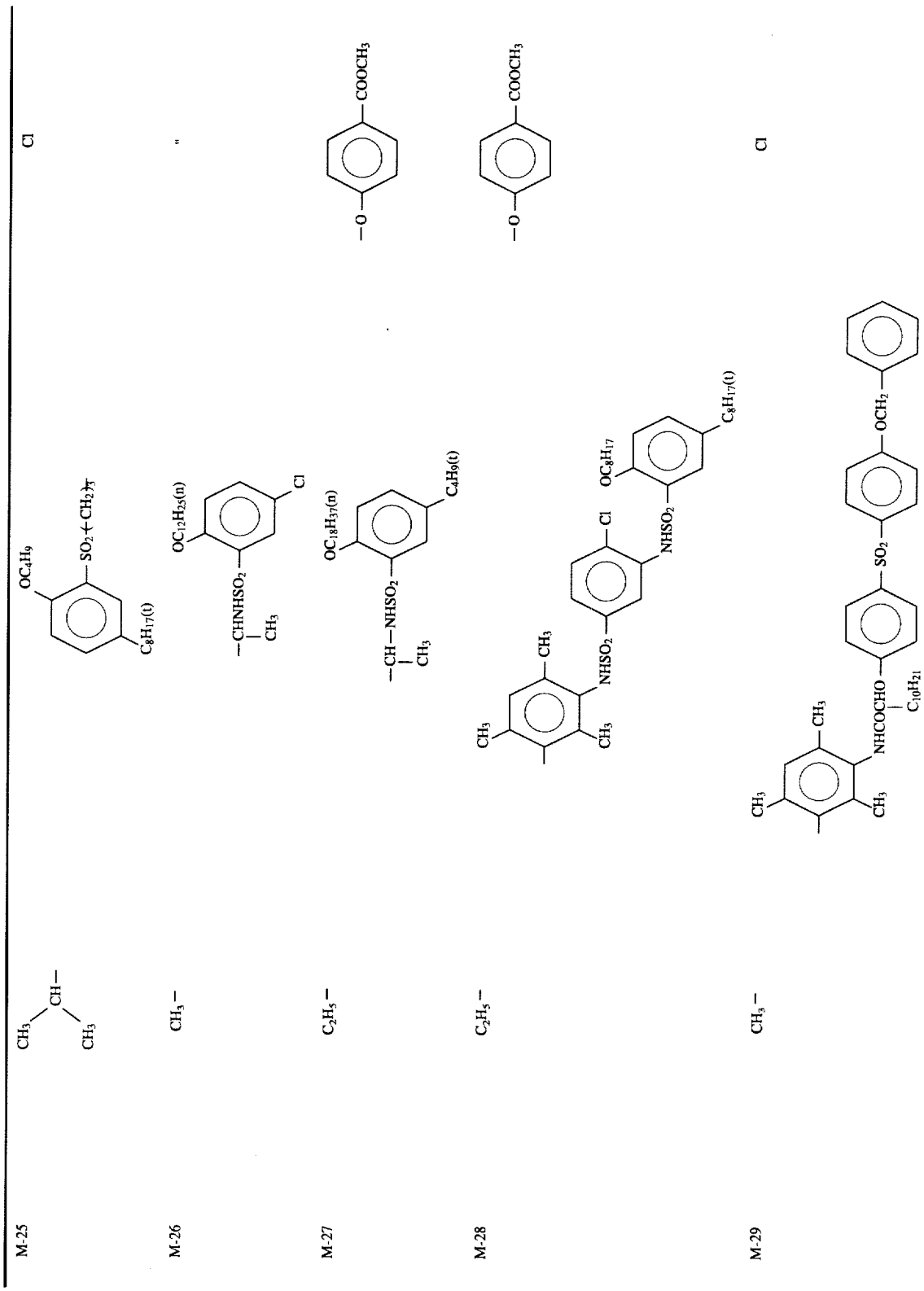

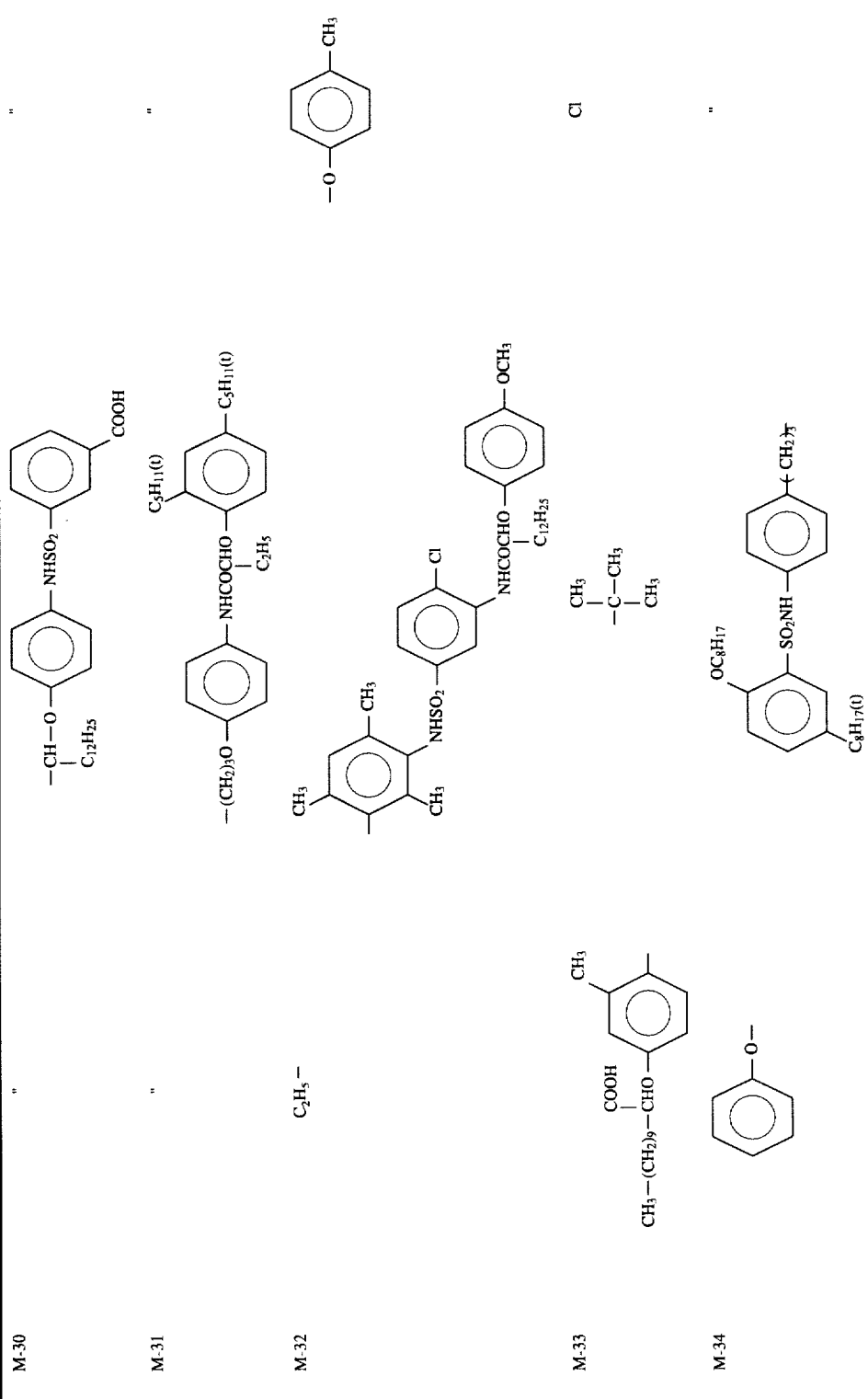

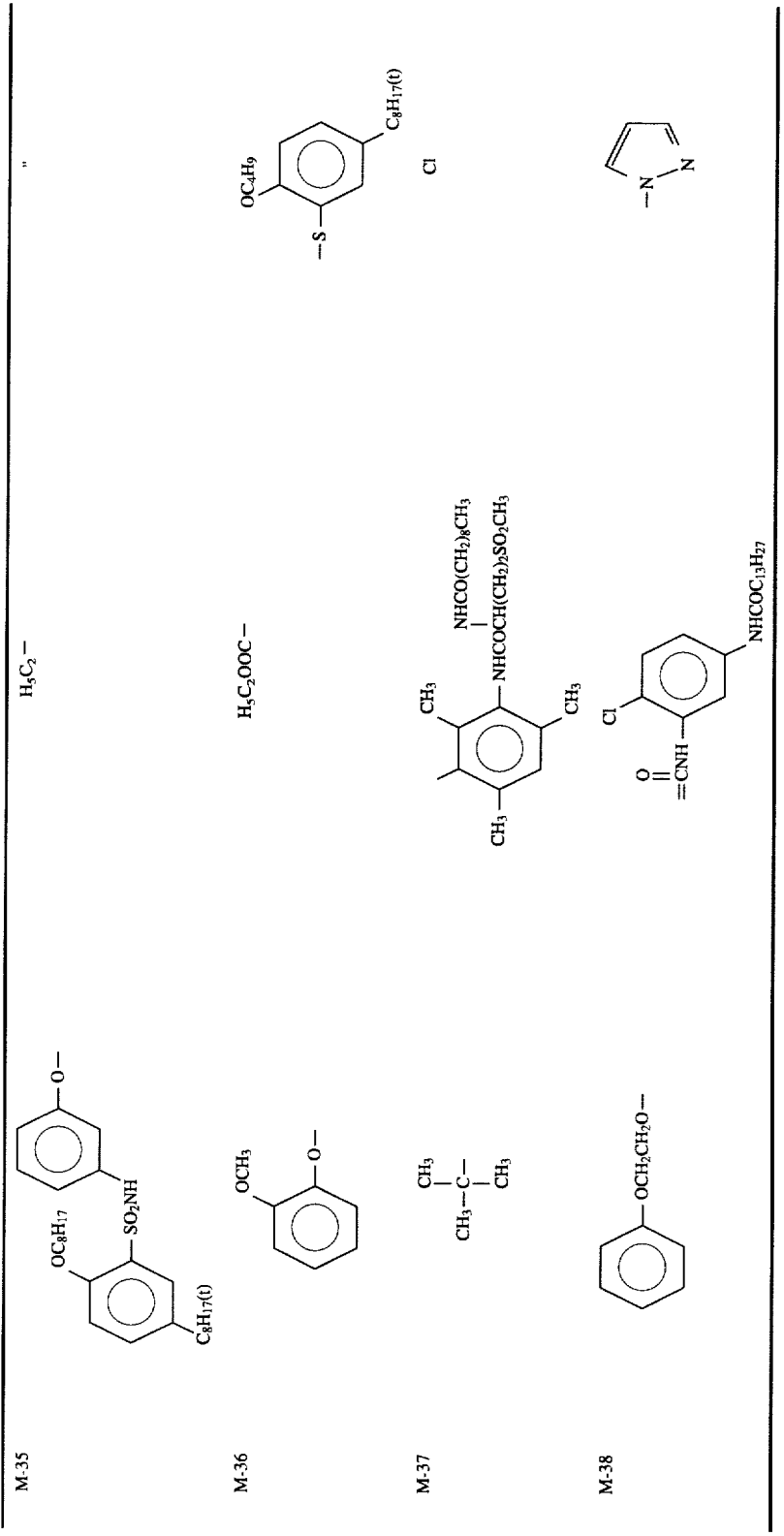

Couplers represented by formula (M) can be synthesized by methods described in, for example, U.S. Pat. Nos. 4,540,654 and 4,705,863, JP-A Nos. 65245/1986, 209457/1987, and 249155/1987, JP-B No. 27411/1972, and U.S. Pat. No. 3,725,067.

The amount of magenta coupler to be added in the silver halide color photographic materil is generally 0.02 to 2.0 mol, preferably 0.05 to 1.5 mol, more preferably 0.1 to 1.0 mol, per mol of silver halide.

In the present invention, the photographic material is subjected to a color developing process, a desilvering process, and a water-washing process (or a stabilizing treatment).

The color developer to be used in the present invention contains known aromatic primary amine color-developing agents. Preferred examples are p-phenylenediamine derivatives, and as representative examples thereof can be mentioned N,N-diethyl-p-phenylenediamine, 2-amino-5-diethylaminotoluene, 2-amino-5-(N-ethyl-N-laurylamino)toluene, 4-[N-ethyl-N-(β-hydroxyethyl)amino]-aniline, 2-methyl-4-[N-ethyl-N-(β-hydroxyethyl)amino]-aniline, 4-amino-3-methyl-N-ethyl-N-[β-(methanesulfonamido)ethyl]-aniline, N-(2-amino-5-diethylaminophenylethyl)methanesulfonamide, N,N-dimethyl-p-phenylenediamine, 4-amino-3-methyl-N-ethyl-N-methoxyethylaniline, 4-amino-3-methyl-N-ethyl-N-β-ethoxyethylaniline, and 4-amino-3-methyl-N-ethyl-N-β-butoxyethylaniline. Among them, 4-amino-3-methyl-N-ethyl-N-[β-(methanesulfonamido)ethyl]-aniline is particularly preferable.

These p-phenylenediamine derivatives may be in the form of salts such as sulfates, hydrochloride, sulfites, and p-toluenesulfonates. The amount of aromatic primary amine developing agent to be used is preferably about 0.1 g to about 20 g, more preferably about 0.5 g to about 10 g, per liter of color developer.

The compound of the present invention is useful when its concentration in a replenishing solution is preferably 8 g/l or more, more preferably 9 g/l or more. The effect of the present invention can be attained by using 4-amino-3-methyl-N-ethyl-N-[β-(methanesulfonamido)ethyl]-aniline.

In practicing the present invention, remarkable effects can be attained in the case of using a color developer substantially free from benzyl alcohol. Herein the term "substantially free from" means that the concentration of benzyl alcohol is preferably 2.0 ml/l or below, more preferably 0.5 ml/l or below, and most preferably benzyl alcohol is not contained at all.

It is more preferable that the color developer for use in this invention is substantially free from sulfite ions (herein "substantially free from" means that the concentration of sulfite ions is $3.0 \times 10^{-3}$ mol/l or below), in order to suppress the variation of photographic properties due to the continuous processing and to attain the effects of the invention more remarkably. More preferably, the concentration of sulfite ions is $1.0 \times 10^{-3}$ mol/l or below, and most preferably sulfite ions are not contained at all. However, in the present invention, a little amount of sulfite ions contained in a processing solution kit having condensed developing agent before to use in order to prevent the oxidation of said kit is excluded.

Preferably, the color developer to be used in the present invention is substantially free from sulfite ions, and more preferably, in addition thereto it is substantially free from hydroxylamine (herein "substantially free from hydroxylamine" means that preferably the concentration of hydroxylamine is $5.0 \times 10^{-3}$ mol/l or below), in order to suppress the variation of photographic properties due to the changing of concentration of hydroxylamine. Most preferably hydroxylamine is not contained at all.

It is more preferable that the color developer to be used in the present invention contains an organic preservative instead of above-described hydroxylamine or sulfite ions.

Herein the term "organic preservative" refers to organic compounds that generally, when added to the processing solution for the color photographic material, reduce the speed of deterioration of the aromatic primary amine color-developing agent. That is, organic preservatives include organic compounds having a function to prevent the color developing agent from being oxidized, for example, with air, and in particular, hydroxylamine derivatives (excluding hydroxylamine, hereinafter the same being applied), hydroxamic acids, hydrazines, hydrazides, phenols, α-hydroxyketones, α-aminoketones, saccharides, monoamines, diamines, polyamines, quaternary ammonium salts, nitroxyradicals,-alcohols, oximes, diamide compounds, and condensed cyclic amines are effective organic preservatives. These are disclosed, for example, JP-B No. 30496/1973, JP-A Nos. 143020/1977, 4235/1988, 30845/1988, 21647/1988, 44655/1988, 53551/1988, 43140/1988, 56654/1988, 58346/1988, 43138/1988, 146041/1988, 44657/1988, and 44656/1988, U.S. Pat. Nos. 3,615,503 and 2,494,903, and JP-A Nos. 97953/1989, 186939/1989, 186940/1989, 187557/1989, and 306422/1990. As the other preservative, various metals described in JP-A Nos. 44148/1982 and 53749/1982, salicylic acids described in JP-A No. 180588/1984, amines described in JP-A Nos. 239447/1988, 128340/1988, 186939//1989, and 187557/1989, alkanolamines described in JP-A No. 3532/1979, polyethyleneimines described in JP-A No. 94349/1981, aromatic polyhydroxyl compounds described in U.S. Pat. No. 3,746,544 maybe included, if needed. It is particularly preferable the addition of alkanolamines, such as triethanolamine, dialkylhydroxylamines, such as N,N-diethylhydroxylamine and N,N-di(sulfoethyl)hydroxylamine, hydrazine derivatives (excluding hydrazine), such as N,N-bis(carboxymethyl)hydrazine, or aromatic polyhydroxyl compounds, such as sodium catechol-3,5-disulfonate.

In particular, the use of alkanolamines in combination with dialkylhydroxylamine and/or hydrazine derivatives is more preferable in view of stability improvement of the color developer resulting its stability improvement during the continuous processing.

In the present invention, the color developer preferably contains chloride ions in an amount of $3.0 \times 10^{-2}$ to $1.5 \times 10^{-1}$ mol/l, more preferably $3.5 \times 10^{-2}$ to $1 \times 10^{-1}$ mol/l. When the concentration of chloride ions exceeds $1.5 \times 10^{-1}$ mol/l, such a defect as to retard the developing occurs, which is not preferable to attain the effect of the present invention of rapid processing and high maximum density. A concentration less than $3.0 \times 10^{-2}$ is not preferably in view of preventing fogging.

In the present invention, the color developer preferably contains bromide ions in an amount of $3 \times 10^{-5}$ to $1 \times 10^{-3}$ mol/l, more preferably $5.0 \times 10^{-5}$ to $5 \times 10^{-4}$ mol/l. When the concentration of bromide ions exceeds $1 \times^{-3}$ mol/l, developing is retarded, resulting maximum density and sensitivity being lowered, and when the concentration is less than $3.0 \times 10^{-5}$ mol/l, fogging cannot be prevented sufficiently.

Herein, chloride ions and bromide ions may be added directly to the color developer, or they may be allowed to dissolve out from the photographic material in the color developer at the development processing.

If chloride ions are added directly to the color developer, as the chloride ion-supplying material can be mentioned sodium chloride, potassium chloride, ammonium chloride, lithium chloride, magnesium chloride, and calcium chloride. Further, they may be supplied from a fluorescent brightening agent that is added to the color developer.

As the bromide ion-supplying material can be mentioned sodium bromide, potassium bromide, ammonium bromide, lithium bromide, calcium bromide, and magnesium bromide.

When chloride ions and bromide ions are allowed to dissolve out from the photographic material in the color developer, both the chloride ions and bromide ions may be supplied from the emulsion or a source other than the emulsion.

Preferably the pH of the color developer to be used in the present invention is in the range of 9 to 12, more preferably 9 to 11.0, and other known compounds that are components of a conventional developing solution can be contained in the color developer.

In order to keep the above pH, it is preferable to use various buffers. As buffers, use can be made, for example, carbonates, phosphates, borates, tetraborates, hydroxylbenzoates, glycyl salts, N,N-dimathylglycinates, leucinates, norleucinates, guanine salts, 3,4-dihydroxyphenylalanine salts, alanine salts, aminobutyrates, 2-amino-2-methyl-1,3-propandiol salts, valine salts, proline salts, trishydroxyaminomethane salts, and lysine salts. It is particularly preferable to use carbonates, phosphates, tetraborates, and hydroxybenzoates as buffers, because they have advantages that they are excellent in solubility and in buffering function in the high pH range of a pH 9.0 or higher, they do not adversely affect the photographic function (for example, to cause fogging), and they are inexpensive.

As specified samples of buffer, there are included sodium carbonate, potassium carbonate, sodium bicarbonate, potassium bicarbonate, trisodium phosphate, tripotassium phosphate, disodium phosphate, dipotassium phosphate, sodium borate, potassium borate, sodium tetraborate (borax), potassium tetraborate, sodium o-hydroxybenzoate (sodium salicylate), potassium o-hydroxybenzoate, sodium 5-sulfo-2-hydroxybenzoate (sodium 5-sulfosalicylate), and potassium 5-sulfo-2-hydroxybenzoate (potassium 5-sulfosalicylate). However, the present invention is not limited to these compounds.

The amount of buffer to be added to the color developer is preferably 0.1 mol/l or more, and particularly preferably 0.1 to 0.4 mol/l.

In addition to the color developer can be added various chelating agents to prevent calcium or magnesium from precipitating or to improve the stability of the color developer. Specific examples are shown below: nitrilotriacetic acid, diethylenetriaminepentaacetic acid, ethylenediaminetetraacetic acid, N,N,N-trimethylenephosphonic acid, ethylenediamine-N,N,N',N'-tetramethylenephosphonic acid, transcyclohexanediaminetetraacetic acid, 1,2-diaminopropanetetraacetic acid, glycol ether diaminetetraacetic acid, ethylenediamine-ortho-hydroxyphenylacetic acid, 2-phosphonobutane-1,2,4-tricarboxylic acid, 1-hydroxyethylidene-1,1-diphosphonic acid, N,N,-bis(2-hydroxybenzyl)ethylene-diamine-N,N'-diacetic acid, and hydroxyethyliminodiacetic acid. If necessary, two or more of these chelating agents may be used together.

With respect to the amount of these chelating agents to be added, it is good if the amount is enough to sequester metal ions in the color developer. The amount, for example, is on the order of 0.1 g to 10 g per liter.

If necessary, any development accelerator can be added to the color developer.

As development accelerators, the following can be added as desired: thioether compounds disclosed, for example, in JP-B Nos. 16088/1962, 5987/1962, 7826/1963, 12380/1969, and 9019/1970, and U.S. Pat. No. 3,813,247; p-phenylenediamine compounds disclosed in JP-A Nos. 49829/1977 and 15554/1975; quaternary ammonium salts disclosed, for example, in JP-A No. 137726/1975, JP-B No. 30074/1969, and JP-A Nos. 156826/1981 and 43429/1977; amine compounds disclosed, for example, in U.S. Pat. Nos. 2,494,903, 3,128,182, 4,230,796, and 3,253,919, JP-B No. 11431/1966, and U.S. Pat. Nos. 2,482,546, 2,596,926, and 3,582,346; polyalkylene oxides disclosed, for example, in JP-B Nos. 16088/1962 and 25201/1967, U.S. Pat. No. 3,128,183, JP-B Nos. 11431/1966 and 23883/1967, and U.S. Pat. No. 3,532, 501; 1-phenyl-3-pyrazolidones, and imidazoles. With respect to benzyl alcohol, it is same as the above-described.

In the present invention, if necessary, any antifoggant can be added. As antifoggants, use can be made of alkali metal halides, such as sodium chloride, potassium bromide, and potassium iodide, and organic antifoggants. As typical organic antifoggants can be mentioned, for example, nitrogen-containing heterocyclic compounds, such as benzotriazole, 6-nitrobenzimidazole, 5-nitroisoindazole, 5-methylbenzotriazole, 5-nitrobenzotriazole, 5-chloro-benzotriazole, 2-thiazolylbenzimidazole, 2-thiazolylmethyl-benzimidazole, indazole, hydroxyazaindolizine, and adenine.

It is preferable that the color developer that is adaptable in the present invention contains a fluorescent brightening agent. As the fluorescent brightening agent, 4,4'-diamino-2, 2'-disulfostilbene compounds are preferable, which will be added in an amount of 0 to 5 g/l, preferably 0.1 to 4 g/l.

If required, various surface-active agents, such as alkylsulfonic acids, arylsulfonic acids, aliphatic carboxylic acids, aromatic carboxylic acids, and polyalkyleneimines may be added.

Further, in the present invention, when the color developer contains thiosulfate radicals of, for example $1\times 10^{-5}$ mol/l or more, further $1\times 10^{-4}$ or more, particularly $2\times 10^{-4}$ to $1\times 10^{-3}$ mol/l, the effect of the present invention can be attained even in the case wherein the color developer is contaminated by the components of following bath such as thiosulfate and the like.

The processing temperature of the color developer adaptable to the present invention is 20° to 50° C., preferably 30° to 40° C., and most preferably 37° to 40° C. The processing time is 20 sec to 5 min, and preferably 25 sec to 1 min. Although it is preferable that the replenishing amount is as small as possible, it is suitable that the replenishing amount is 20 to 600 ml, preferably 30 to 200 ml, more preferably 40 to 100ml, per $m^2$ of the photographic material.

With respect to the color developer of the present invention, for details other than the above described those of a usual color developer can be adapted.

The photographic material is generally subjected to a desilvering process after color development. The desilvering process can be carried out by a bleaching process and a fixing process, separately, or carried out at the same time (bleach-fixing process). Further, to quicken the process bleach-fixing may be carried out after the bleaching process. In accordance with the purpose, the process may be arbitrarily carried out using a bleach-fixing bath having two successive tanks, or a fixing process may be carried out before the bleach-fixing process, or a bleaching process may be carried out after the bleach-fixing process.

As the bleaching agent to be used in a bleaching solution and a bleach-fix solution, use can be made of, for example, ion salts, compounds of polyvalent metals, such as iron (III), cobalt (III), chromium (VI), and copper (II), peracids, quinones, and nitro compounds. As typical bleaching agents, use can be made of iron chlorides, ferricyanides, dichromates, organic complex salts of iron (III) (e.g., complex salts of aminopolycarboxylic acid, such as ethylenediaminetetraacetic acid, diethylenetriaminepentaacetic acid, cyclohexanediaminetetraacetic acid, methyliminodiacetic acid, 1,3-diaminopropanetetraacetic acid, and glycoletherdiaminetetraacetic acid), persulfates, bromates, permanganates, and nitrobenzenes. Of these, aminopolycarboxylic acid complex salts of iron (III), including ethylenediaminetetraacetic acid iron (III) complex salts and 1,3-diaminopropanetetraacetic acid iron (III) complex salt are preferable in view of the rapid processing and the prevention of environmental pollution. Further, aminopolycarboxylic acid iron (III) complex salts are particularly useful in a bleaching solution as well as a bleach-fix solution. The bleaching solution or the bleach-fix solution using these aminopolycarboxylic acid iron (III) complex salts is generally used in pH 3 to 8.

Known additives, for example, a rehalogenating agent, such as ammonium bromide and ammonium chloride, a pH buffer such as ammonium nitrare, and a metal-corrosion-preventing agent such as ammonium sulfate can be added in the bleaching solution or the bleach-fix solution.

In addition to the above-described compounds, an organic acid is preferably contained in the bleaching solution and the bleach-fix solution. Particularly preferable organic acids include compounds having an acid dissociation constant (pKa) of 2 to 5.5, and specifically acetic acid and propionic acid are preferable.

Although as the fixing agents to be used in the fixing solution and bleach-fix solution use can be made of thiosulfates, thiocyanates, thioether compounds, thioureas, and a large amount of iodide salts, the use of thiosulfate is general, particularly ammonium thiosulfate can be used most widely. Further, combination use of thiosulfate with thiocyanate, thioether compound, or thiourea is also preferable.

As a preservative for the fixing solution and the bleach-fixing solution, sulfites, bisulfites, carbonyl-bisulfic acid adduct or sulfinic acid compounds described in European Patent No. 294769A are preferable. Further, it is preferable to add various aminopolycarboxylic acids or organic phosphonic acids (e.g., 1-hydroxyethylidene-1,1-diphosphonic acid and N,N,N',N'-ethylenediaminetetraohosphonic acid) in the fixing solution and the bleach-fix solution for the purpose to stabilize the solution.

Further, in the fixing solution and the bleach-fixing solution, various fluorescent brightening agents, antifoamers, surface-active agents, poly(vinyl pyrrolidone), and methanol can be included.

In the bleaching solution, the bleach-fix solution, and/or bath preceding them, various compounds may be used as a bleach-accelerating agent, according to a need. As specific examples of useful bleach-accelerating agents, use can be made of, for example, compounds having a mercapto group or a disulfido group, described in U.S. Pat. No. 3,893,858, West German Patent No. 1,290,812, and JP-A No. 95630/1978, and *Research Disclosure* No. 17129 (July 1978), thiazolizine compounds described in JP-A No. 140129/1975, thiourea compounds described in U.S. Pat. No. 3,706,561, iodide salts described in JP-A No. 16235/1983, polyoxyethylene compounds described in West German Patent No. 2,748,430, polyamine compounds described in JP-B No. 8836/1970, and bromide ions. Among them, compounds having a mercapto group or disulfide group are preferable in view of large accelerating effect, in particular, compounds described in U.S. Pat. No. 3,893,858, West German Patent No. 1,290,812, and JP-A No. 95630/1978 are preferable. Further, the compound described in U.S. Pat. No. 4,552,834 is also preferanle. These bleach-accelerating agents may be added in the photographic material. These bleach-accelerating agents are particularly effective for bleach-fixing a color photographic material for photography.

The shorter the total time of the desilvering step is, the more preferable it is within the range wherein silver retention does not occur. Preferably it is 10 sec to 3 min, more preferably 20 sec to 2 min. The processing temperature is 25° to 50° C., preferably 35° to 45° C. In the preferable temperature range, the desilvering speed is improved and occurrence of stain after the processing is effectively prevented.

In the desilvering step, preferably the stirring is enhanced as much as possible. Specific techniques for enhancing the stirring that can be mentioned include a method described in JP-A No. 183460/1987 or No. 183461/1987, wherein a jet of a processing solution is caused to impinge upon the emulsion surface of a photographic material; a method described in JP-A No. 183461/1987, wherein a rotating means is used for increasing the stirring effect; a method wherein a photographic material is moved with a wiper blade provided in a solution in contact with the emulsion surface, to make the solution near the emulsion surface turbulent, thereby improving the stirring effect; and a method wherein the circulated flow rate of all the processing solution is increased. Such a means of improving stirring is effective for any of a bleaching solution, a bleach-fix solution, and a fixing solution. It is considered that the improvement of stirring quickens the supply of a bleaching agent and a fixing agent into emulsion layers, and as a result the speed of desilvering is increased. Further when a bleach accelerator is used, the above means of improving stirring is more effective, increases the accelerating effect noticeably; and it can cancel the fixing-hindrance effect of the bleach accelerator.

The automatic processor to be used for the photographic material according to the present invention is preferably provided with a photographic material transporting means described in JP-A Nos. 191257/1985, 191258/1985, and 191259/1985. As is described in JP-A No. 191257/1985, such a transporting means can reduce considerably the carry-over of the processing solution from a preceding bath to the succeeding bath, and it is high in the effect of preventing the performance of the processing solution from being deteriorated. Such an effect is particularly efficacious in shortening the processing time in each step and in reducing the replenishing amount of the processing solution.

Generally, the color photographic material of the present invention is subjected to a washing step after the desilvering process. Instead of the washing step, a stabilizing step can be carried out. In such a stabilizing process, any of known methods described in JP-A Nos. 8543/1982, 14834/1983, and 220345/1985 can be used. A washing step/stabilizing step, wherein a stabilizing bath containing a dye stabilizer and a surface-active agent that is typically used for processing a photographing color photographic material is used as a final bath, can be carried out.

The washing solution and the stabilizing solution can contain a water softener, such as an inorganic phosphoric acid, polyaminocarbonic acid, and an organic aminophosphonic acid; a metal salt such as an Mg salt, an Al salt, and a Bi salt; a surface-active agent; and a hardening agent.

The amount of washing water in the washing step can be set over a wide range, depending on the characteristics of the photographic material (e.g., the characteristics of the material used, such as couplers), the usage of the photographic material, the washing water temperature, the number of the washing water tanks (stages), the type of replenishing, such as the countercurrent type or of the down flow type, and other various conditions. Further, to solve such problems as the propagation of bacteria when the amount of washing water is decreased greatly at a countercurrent flow system and the adhering of suspended matter to the photographic material, the method for reducing calcium ions and magnesium ions, described in JP-A No. 288838, can be used quite effectively. Also, isothiazolone compounds and cyabendazoles described in JP-A No. 8542/1982, chlorine-type disinfectant such as chlorinated sodium isocyanurate, benzotriazoles, and other bactericides described by Hiroshi Horiguchi in *Bokin Bobai-zai no Kagaku*, (1986) published by Sankyo-Shuppan, *Biseibutsu no Mekkin, Sakkin, Bobaigijutsu* (1982) edited by Eiseigijutsu-kai, published by Kogyo-Gijutsu-kai, and in *Bokin Bobaizai Jiten* (1986) edited by Nihon Bokin Bobai-gakkai, can be used.

The pH of the washing water used in the washing step is 4 to 9, preferably 5 to 8. The washing water temperature and the washing time to be set may vary depending, for example, on the characteristics and the application of the photographic material, and they are generally selected in the range of 15° to 45° C. for sec to 10 min, and preferably in the range of 25° to 40° C. for 30 sec to 5 min.

As dye-stabilizing agents to be able to use in a stabilizing solution, aldehydes, such as formalin and gultalaldehyde, N-methylol compounds, hexamethylenetetramine, and aldehyde-sulfic acid adduct can be mentioned. Further, the stabilizing solution can contain pH controlling buffer, such as boric acid and sodium hydride, 1-hydroxyethylidene-1, 1-diphosphonic acid, chelating agent, such as ethylenediaminetetraacettic acid, sulfulation-preventer, such as alkanolamine, fluorescent brightening agent, and antimold agent.

The over-flowed solution due to the above-mentioned replenishing of washing solution and/or stabilizing solution may be reused in other steps, such as a desilvering step.

In the processing using an automatic processor, it is preferable to correct the concentration of processing solution by adding water when concentration due to evaporation occurs.

The silver halide color photographic material of the present invention may contain therein a color-developing agent for the purpose of simplifying and quickening the process. To contain such a color-developing agent, it is preferable to use a precursor for color-developing agent. For example, indoaniline-type compounds described in U.S. Pat. No. 3,342,597, Schiff base-type compounds described in U.S. Pat. No. 3,342,599 and *Research Disclosure* Nos. 14850 and 15159, aldol compounds described in *Research Disclosure* No. 13924, and metal salt complexes described in U.S. Pat. No. 3,719,492, and urethane-type compounds described in JP-A No. 135628/1978 can be mentioned.

For the purpose of accelerating the color development, the silver halide color photographic material may contain, if necessary, various 1-phenyl-3-pyrazolicones. Typical compounds are described in JP-A Nos. 64339/1981, 144547/1982, and 115438/1983.

The present invention may be adapted in any of photographic materials. In the present invention, as silver halide emulsions and other materials (e.g., additives), photographic constituting layers (e.g., arrangement of layers), processing processes and additives for processing there can be preferably used those described in the following patent, particularly European Patent EP 0,355,660A2 (JP-A No. 107011/1989).

| Element constituting photographic material | JP-A No. 215272/1987 | JP-A No. 33144/1990 | EP 0,355,660A2 |
|---|---|---|---|
| Silver halide emulsion | p. 10 upper right column line 6 to p. 12 lower left column line 5, and p. 12 lower right column line 4 from the bottom to p. 13 upper left column line 17 | p. 28 upper right column line 16 to p. 29 lower right column line 11 and p. 30 lines 2 to 5 | p. 45 line 53 to p. 47 line 3 and p. 47 lines 20 to 22 |
| Solvent for silver halide | p. 12 lower left column line 6 to 14 and p. 13 upper left column line 3 from the bottom to p. 18 lower left column last line | — | — |
| Chemical sensitizing agent | p. 12 lower left column line 3 from the bottom to lower right column line 5 from the bottom and p. 18 lower right column line 1 to p. 22 upper right column line 9 from the bottom | p. 29 lower right column line 12 to last line | p. 47 lines 4 to 9 |
| Spectral sensitizing agent (method) | p. 22 upper right column line 8 from the bottom to p. 38 last line | p. 30 upper left column lines 1 to 13 | p. 47 lines 10 to 15 |
| Emulsion stabilizer | p. 39 upper left column line 1 to p. 72 upper right column last line | p. 30 upper left column line 14 to upper right column line 1 | p. 47 lines 16 to 19 |
| Developing accelerator | p. 72 lower left column line 1 to p. 91 upper right | — | — |

-continued

| Element constituting photographic material | JP-A No. 215272/1987 | JP-A No. 33144/1990 | EP 0,355,660A2 |
|---|---|---|---|
| | column line 3 | | |
| Color coupler (Cyan, Magenta, and Yellow coupler) | p. 91 upper right column line 4 to p. 121 upper left column line 6 | p. 3 upper right column line 14 to p. 18 upper left column last line and p. 30 upper right column line 6 to p. 35 lower right column line 11 | p.4 lines 15 to 27, p.5 line 30 to p. 28 last line, p. 45 lines 29 to 31 and p. 47 line 23 to p. 63 line 50 |
| Color Formation-strengthen agent | p. 121 upper left column line 7 to p. 125 upper right column line 1 | — | — |
| Ultraviolet absorbing agent | p. 125 upper right column line 2 to p. 127 lower left column last line | p. 37 lower right column line 14 to p. 38 upper left column line 11 | p. 65 lines 22 to 31 |
| Discoloration inhibitor (Image-dye stabilizer) | p. 127 lower right column line 1 to p. 137 lower left column line 8 | p. 36 upper right column line 12 to p. 37 upper left column line 19 | p. 4 line 30 to p. 5 line 23, p. 29 line 1 to p. 45 line 25 p. 45 lines 33 to 40 and p. 65 lines 2 to 21 |
| High-boiling and/or low-boiling solvent | p. 137 lower left column line 9 to p. 144 upper right column last line | p. 35 lower right column line 14 to p. 36 upper left column line 4 | p. 64 lines 1 to 51 |
| Method for dispersing additives for photograph | p. 144 lower left column line 1 to p. 146 upper right column line 7 | p. 27 lower right column line 10 to p. 28 upper left column last line and p. 35 lower right column line 12 to p. 36 upper right column line 7 | p. 63 line 51 to p. 64 line 56 |
| Film Hardener | p. 146 upper right column line 8 to p. 155 lower left column line 4 | — | — |
| Developing Agent precursor | p. 155 lower left column line 5 to p. 155 lower right column line 2 | — | — |
| Compound releasing development inhibitor | p. 155 lower right column lines 3 to 9 | — | — |
| Support | p. 155 lower right column line 19 to p. 156 upper left column line 14 | p. 38 upper right column line 18 to p. 39 upper left column line 3 | p. 66 line 29 to p. 67 line 13 |
| Constitution of photosensitive layer | p. 156 upper left column line 15 to p. 156 lower right column line 14 | p. 28 upper right column lines 1 to 15 | p. 45 lines 41 to 52 |
| Dye | p. 156 lower right column line 15 to p. 184 lower right column last line | p. 38 upper left column line 12 to upper right column line 7 | p. 66 lines 18 to 22 |
| Color-mix inhibitor | p. 185 upper left column line 1 to p. 188 lower right column line 3 | p. 36 upper right column lines 8 to 11 | p. 64 line 57 to p. 65 line 17 |
| Gradation controller | p. 188 lower right column line 4 to 8 | — | — |
| Stain inhibitor | p. 188 lower right column line 9 to p. 193 lower right column line 10 | p. 37 upper left column last line to lower right column line 13 | p. 65 line 32 to p. 66 line 1 |
| Surface-active agent | p. 201 lower left column line 1 to p. 210 upper right column last line | p. 18 upper right column line 1 to p. 24 lower right column last line and p. 27 lower left column line 10 from the bottom to lower right column line 9 | — |
| Fluorine-containing agent (As Antistatic agent, coating aid, lubricant, adhesion inhibitor, or the like) | p. 210 lower left column line 1 to p. 222 lower left column line 5 | p. 25 upper left column line 1 to p. 27 lower right column line 9 | — |
| Binder (Hydrophilic colloid) | p. 222 lower left column line 6 to p. 225 upper left column last line | p. 38 upper right column lines 8 to 18 | p. 66 lines 23 to 28 |
| Thickening agent | p. 225 upper right column line 1 to p. 227 upper | — | — |

| Element constituting photographic material | JP-A No. 215272/1987 | JP-A No. 33144/1990 | EP 0,355,660A2 |
|---|---|---|---|
| Antistatic agent | right column line 2 p. 227 upper right column line 3 to p. 230 upper left column line 1 | — | — |
| Polymer latex | p. 230 upper left column line 2 to p. 239 last line | | |
| Matting agent | p. 240 upper left column line 1 to p. 240 upper right column last line | — | — |
| Photographic processing method (processing process, additive, etc.) | p. 3 upper right column line 7 to p. 10 upper right column line 5 | p. 39 upper left column line 4 to p. 42 upper left column last line | p. 67 line 14 to p. 69 line 28 |

Note: In the cited part of JP-A No. 21572/1987, amendment filed on March 16, 1987 is included. Further, among the above-mentioned couplers, it is preferred to use so called short wavelength-type yellow coupler, described in JP-A Nos. 231451/1988, 123047/1988, 241547/1988, 173499/1989, 213648/1989, and 250944/1989, as a yellow coupler.

Further, as cyan couplers, diphenylimidazole cyan couplers described in JP-A No. 33144/1990, as well as 3-hydroxypyridine cyan couplers described in European Patent EP 0,333,185A2 (in particular one obtained by causing Coupler (42), which is a four-equivalent coupler, to have a chlorine coupling-off group, thereby rendering it two-equivalent, and Coupler (6) and (9), which are listed as specific examples, are preferable) and cyclic active methylene cyan couplers described in JP-A No. 32260/1989 (in particular, specifically listed Coupler Examples 3, 8, and 32 are preferable) are preferably used.

Although, as a silver halide for use in the present invention, for example, silver chloride, silver bromide, silver chlorobromide, silver iodochlorobromide, and silver iodobromide can be used, particularly for the purpose of the present invention, a silver chlorobromide emulsion or a silver chloride emulsion substantially free from silver iodide and having a silver chloride content of 90 mol % or more, preferably 95 mol % or more, particularly preferably 98 mol % or more, is used preferably.

In the photographic material according to the present invention, in order to improve, for example, sharpness of the image, preferably a dye capable of being decolored by processing (in particular an oxonol dye), as described in European Patent EP 0,337,490A2, pages 27 to 76, is added to a hydrophilic colloid layer, so that the optical reflection density of the photographic material at 680 nm may be 0.70 or over, 12 wt % or more (preferably 14 wt % or more) of titanium dioxide the surface of which has been treated with a secondary to quarternary alcohol (e.g., trimethylolethane) or the like is contained in a water-resistant resin layer of the support.

In the photographic material according to the present invention, preferably together with the coupler a color-image preservability-improving compound, as described in European Patent EP 0,277,589A2, is used. Particularly a combination with a pyrazoloazole coupler is preferable.

That is, when a compound (F), which will chemically combine with the aromatic amine developing agent remaining after the color development processing to form a chemically inactive and substantially colorless compound, and/or a compound (G), which will chemically combine with the oxidized product of the aromatic amine color developing agent remaining after the color development processing to form a chemically inactive and substantially colorless compound, are used simultaneously or singly, it is preferable because the occurrence of stain and other side effects, for example, due to the production of a color-formed dye by reaction of the coupler with the color-developing agent or its oxidized product remaining in the film during the storage after the processing, can be prevented.

To the photographic material according to the present invention, a mildew-proofing agent described, for example, in JP-A No. 271247/1988, is preferably added in order to prevent the growth of a variety of mildews and fungi that will propagate in the hydrophilic colloid layer and deteriorate the image thereon.

As a support to be used for the photographic material according to the present invention, a white polyester support for display may be used, or a support wherein a layer containing white pigment is provided on the side that will have a silver halide layer. Further, in order to improve sharpness, preferably an anti-halation layer is applied on the side of the support where the silver halide emulsion layer is applied or the undersurface of the support. In particular, preferably the transmission density of the support is set in the range of 0.35 to 0.8, so that the display can be appreciated through either reflected light or transmitted light.

The photographic material according to the present invention may be exposed to visible light or infrared light. The method of exposure may be low-intensity exposure or high-intensity short-time exposure, and particularly in the later case, the laser scan exposure system, wherein the exposure time per picture element is less than $10^{-4}$ sec is preferable.

When exposure is carried out, the band stop filter, described in U.S. Pat. No. 4,880,726, is preferably used. Thereby light color-mixing is eliminated and the color reproduction is remarkably improved.

According to the present invention, the change of photographic properties due to the fluctuation of replenishing amount of color developer and the contamination of color developer can be restrained remarkably by using the thiourea compound represented by formula (I).

Further, the problems which are caused by using a pyrazoloazole coupler as magenta coupler can be improved by using said thiourea compound.

The present invention will be described in detail in accordance with examples, but the invention is not limited to these examples.

EXAMPLE 1

After the surface of a paper support, whose both surfaces were laminated with polyethylene, was subjected to corona discharge treatment, a gelatin undercoat layer containing sodium dodecylbenzenesulfonate was provided thereon, and various photographic constitutional layers were applied, to prepare a multi-layer color photographic printing paper A having the below-given layer constitution. The coating solution were prepared as follows:

Preparation of the Fifth Layer Coating Solution 50.0 Milliliters of ethyl acetate and 14.0 g of Solvent (Solv-6) were added to 32.0 g of Cyan Coupler (ExC), 3.0 g of Image-dye Stabilizer (Cpd-2), 2.0 g of Image-dye Stabilizer (Cpd-4), 18.0 g of Image-dye stabilizer (Cpd-6), 40.0 g of Image-dye stabilizer (Cpd-7), and 5.0 g of Image-dye Stabilizer (Cpd-8), to dissolve them, and the solution was added into 500 ml of 20% aqueous gelatin solution containing 8 ml of 10% sodium dodecylbenzenesulfonate, and emulsified and dispersed by a supersonic homogenizer, to prepare an emulsified dispersion. Separately, a silver chlorobromide emulsion (comprising cubic silver halide grains made up of a mixture of a large size emulsion having an average grain size of 0.58 μm and a small size emulsion having an average grain size of 0.45 μm in a molar ratio of 1:4 in terms of silver, wherein the deviation coefficients of the grain size distributions are 0.09 and 0.11, respectively; each of the emulsions has 0.6 mol % of AgBr being localized on the surface of the grains; and the remaining part of grain is made of AgCl) was prepared. Red-sensitive sensitizing dye E, shown below, was added in this emulsion in an amount of $0.9 \times 10^{-4}$ mol to the large size emulsion and $1.1 \times 10^{-4}$ mol to the small size emulsion, per mol of silver, respectively. The chemical ripening of this emulsion was carried out by adding a sulfur sensitizing agent and a gold sensitizing agent. The above-described emulsified dispersion and this red-sensitive silver chlorobromide emulsion were mixed together and dissolved to give the composition shown below, thereby preparing the fifth layer coating solution.

Coating solutions for the first to fourth, and sixth and seventh layers were prepared in the same manner as the fifth layer coating solution. As the gelatin hardener of each layer, 1-hydroxy-3,5-dichloro-s-triazine sodium salt was used. Cpd-10 and Cpd-11, shown below, were added to each layer so that the total amounts thereof might be 25.0 mg/m² and 50.0 mg/m², respectively.

In the silver chlorobromide emulsions of photosensitive emulsion layers, the following spectral sensitizing dyes were used.

Blue-sensitive emulsion layer:

Sensitizing dye A

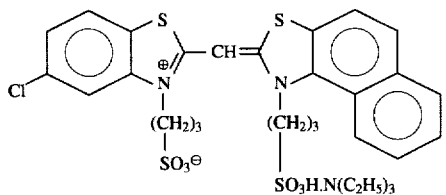

and

Sensitizing dye B

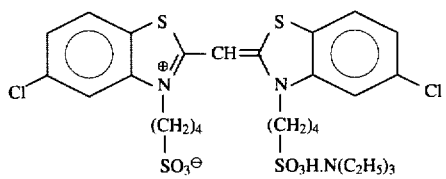

(each $2.0 \times 10^{-4}$ mol to the large size emulsion and $2.5 \times 10^{-4}$ mol to the small size emulsion, per mol of silver halide.)

Green-sensitive emulsion layer:

Sensitizing dye C

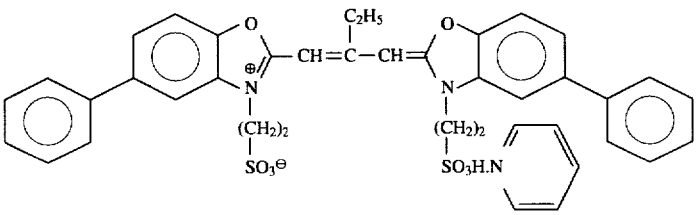

($4.0 \times 10^{-4}$ mol to the large size emulsion and $5.6 \times 10^{-4}$ mol to the small size emulsion, per mol of silver halide) and Sensitizing dye D

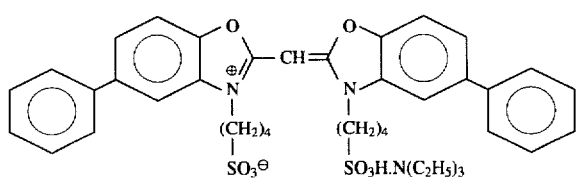

($7.0 \times 10^{-5}$ mol to the large size emulsion and $1.0 \times 10^{-5}$ mol to the small size emulsion, per mol of silver halide)

Red-sensitive emulsion layer:

Sensitizing dye E

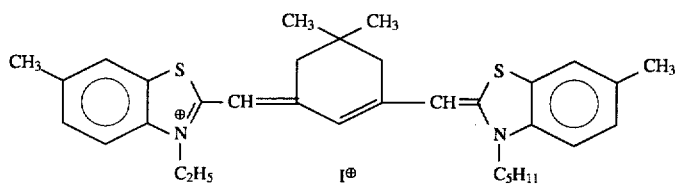

($0.9\times10^{-4}$ mol to the large size emulsion and $1.1\times10^{-4}$ mol to the small size emulsion, per mol of silver halide)

To the red-sensitive emulsion layer, the following compound was added in an amount of $2.6\times10^{-3}$ mol per mol of silver halide:

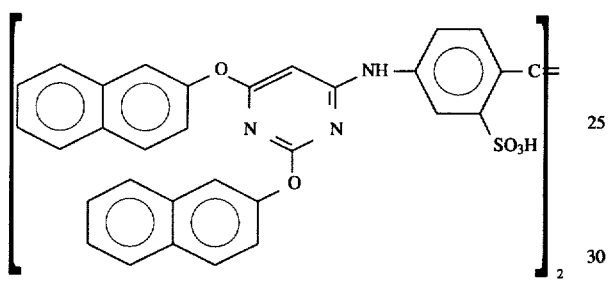

Further, respectively to the blue-sensitive emulsion layer, the green-sensitive emulsion layer, and the red-sensitive emulsion layer, was added 1-(5-methylureidophenyl)-5-mercaptotetrazole in respective amounts of $8.5\times10^{-5}$ mol, $7.7\times10^{-4}$ mol, and $2.5\times10^{-4}$ mol, per mol of the silver halide.

Further, respectively to the blue-sensitive emulsion layer and the green-sensitive emulsion layer, was added 4-hydroxy-6-methyl-1,3,3a,7-tetrazaindene in respective amounts of $1\times10^{-4}$ mol and $2\times10^{-4}$ mol, per mol of the silver halide.

Further, to prevent irradiation, the following dye (the coating amount is indicated in parentheses) was added to the emulsion layers.

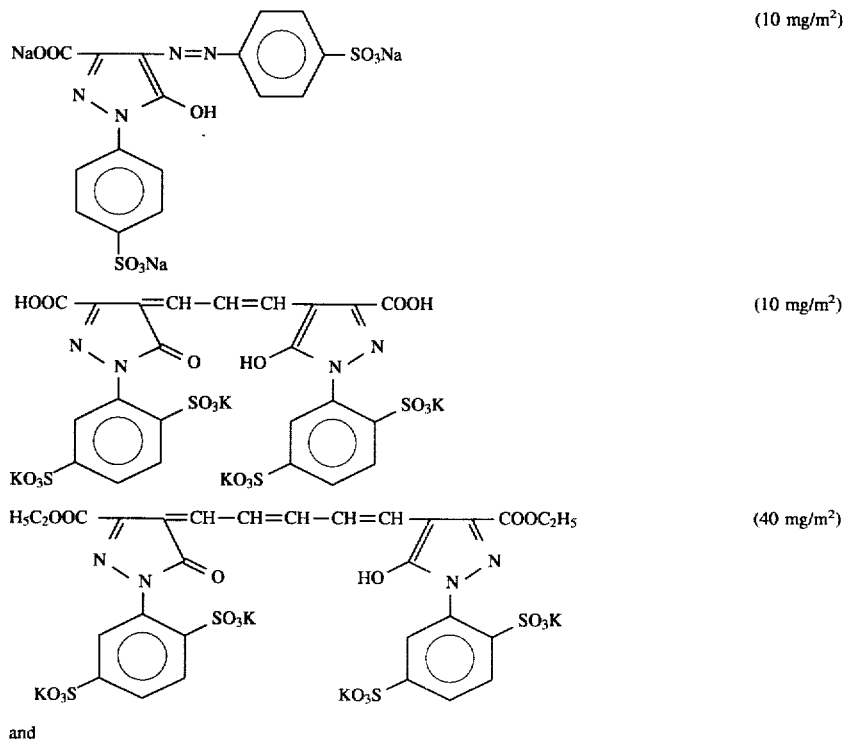

and

-continued

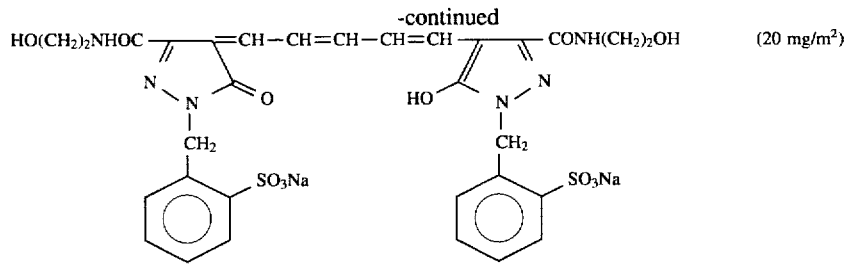

(20 mg/m²)

(Layer Composition)

The layer compositions of the layers are shown below. The numerals indicate coating amounts (g/m²). The coating amount of each of the silver halide emulsions is in terms of silver.

Support

Paper laminated on both sides with polyethylene (a white pigment, $TiO_2$, and a bluish dye, ultramarine, were included in the first layer side of the polyethylene-laminated film)

First Layer (Blue-sensitive emulsion layer)

Silver chlorobromide emulsion (comprising cubic silver halide grains made up of a mixture of a large size emulsion having an average grain size of 0.88 μm and a small size emulsion having an average grain size of 0.70 μm in a molar ratio of 3:7 in terms of silver, wherein the deviation coefficients of the grain size distributions are 0.08 and 0.10 respectively; each of the emulsions has 0.3 mol % of silver bromide being localized on the surface of the grains; and the remaining part of grain is made of silver chloride) 0.30

| Gelatin | 1.86 |
| --- | --- |
| Yellow coupler (ExY) | 0.82 |
| Image-dye stabilizer (Cpd-1) | 0.19 |
| Solvent (Solv-3) | 0.18 |
| Solvent (Solv-7) | 0.18 |
| Image-dye stabilizer (Cpd-7) | 0.06 |

Second Layer (Color-mix preventing layer)

| Gelatin | 0.99 |
| --- | --- |
| Color mix inhibitor (Cpd-5) | 0.08 |
| Solvent (Solv-1) | 0.16 |
| Solvent (Solv-4) | 0.08 |

Third Layer (Green-sensitive emulsion layer)

Silver chlorobromide emulsion (comprising cubic silver halide grains made up of a mixture of a large size emulsion having an average grain size of 0.55 μm and a small size emulsion having an average grain size of 0.39 μm in a molar ratio of 1:3 in terms of silver, wherein the deviation coefficients of the grain size distributions are 0.10 and 0.08 respectively; each of the emulsions has 0.8 mol % of silver bromide being localized on the surface of the grains; and the remaining part of grain is made of silver chloride) 0.12

| Gelatin | 1.24 |
| --- | --- |
| Magenta coupler (ExM) | 0.23 |
| Image-dye stabilizer (Cpd-2) | 0.03 |
| Image-dye stabilizer (Cpd-3) | 0.16 |
| Image-dye stabilizer (Cpd-4) | 0.02 |
| Image-dye stabilizer (Cpd-9) | 0.02 |
| Solvent (Solv-2) | 0.40 |

Fourth Layer (Ultraviolet-absorbing layer)

| Gelatin | 1.58 |
| --- | --- |
| Ultraviolet-absorbing agent (UV-1) | 0.47 |
| Color-mix inhibitor (Cpd-5) | 0.05 |
| Solvent (Solv-5) | 0.24 |

Fifth Layer (Red-sensitive emulsion layer)

Silver chlorobromide emulsion (comprising cubic silver halide grains made up of a mixture of a large size emulsion having an average grain size of 0.58 μm and a small size emulsion having an an average grain size of 0.45 μm in a molar ratio 1:4 in terms of silver, wherein the deviation coefficients of the grain size distributions are 0.09 and 0.11 respectively; each of the emulsions has 0.6 mol % of silver bromide being localized on the surface of the grains; and the remaining part of grain is made of silver chloride) 0.23

| Gelatin | 1.34 |
| --- | --- |
| Cyan coupler (ExC) | 0.32 |
| Image-dye stabilizer (Cpd-2) | 0.03 |
| Image-dye stabilizer (Cpd-4) | 0.02 |
| Image-dye stabilizer (Cpd-6) | 0.18 |
| Image-dye stabilizer (Cpd-7) | 0.40 |
| Image-dye stabilizer (Cpd-8) | 0.05 |
| Solvent (Solv-6) | 0.14 |

Sixth layer (Ultraviolet-absorbing layer)

| Gelatin | 0.53 |
| --- | --- |
| Ultraviolet-absorbing agent (UV-1) | 0.16 |
| Color-mix inhibitor (Cpd-5) | 0.02 |
| Solvent (Solv-5) | 0.08 |

Seventh layer (Protective layer)

| Gelatin | 1.33 |
| --- | --- |
| Acryl-modified copolymer of polyvinyl alcohol (modification degree: 17%) | 0.17 |
| Liquid paraffin | 0.33 |

Compounds used are as follows:

Yellow coupler (ExY)
Mixture (1:1 in molar ratio) of (a) and (b)
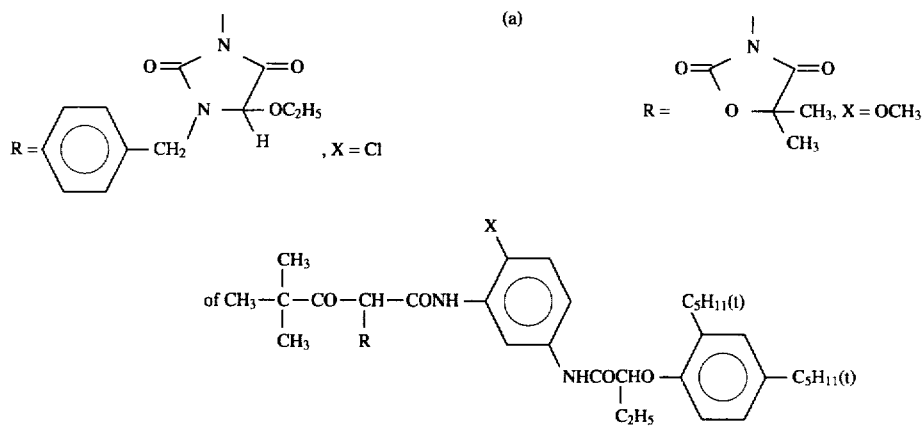
Magenta coupler (ExM)
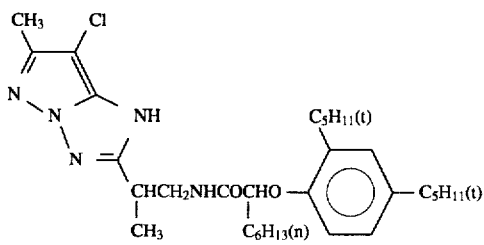
Cyan coupler (ExC)
Mixture (1:1 in molar ratio) of
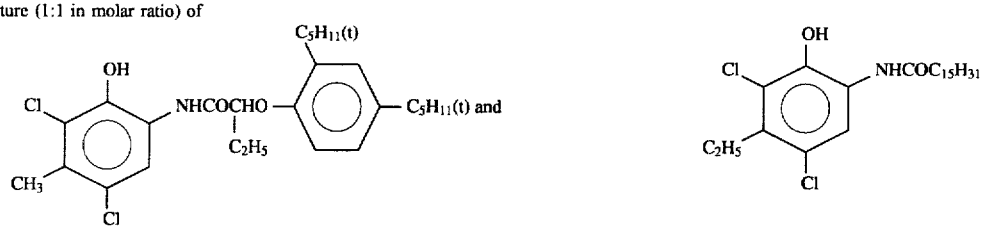
Image-dye stabilizer (Cpd-1)
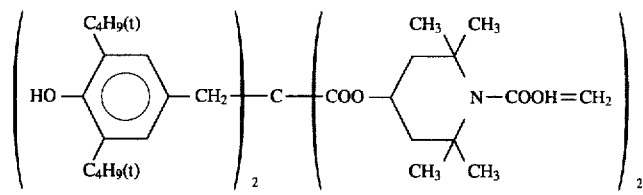
Image-dye stabilizer (Cpd-2)  Image-dye stabilizer (Cpd-3)
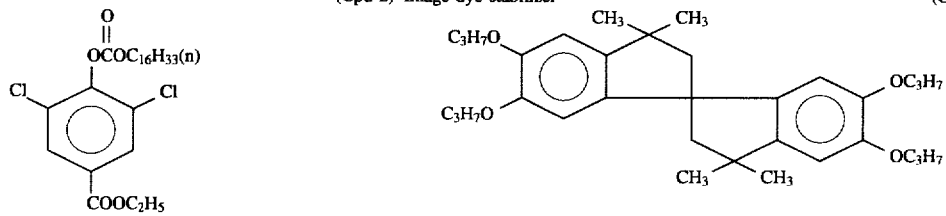

Image-dye stabilizer (Cpd-4)
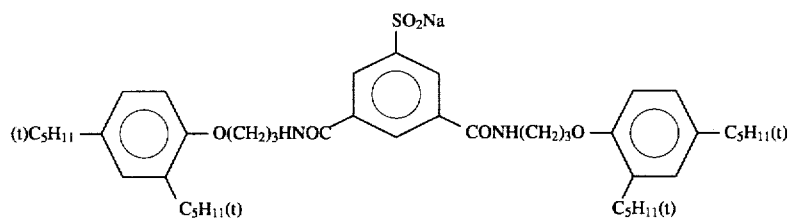
Image-dye stabilizer (Cpd-5)
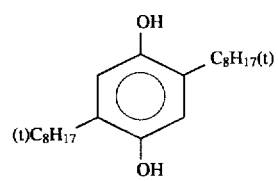
Image-dye stabilizer (Cpd-6)
Mixture ((i):(ii):(iii) = 2:4:4 in weight ratio) of
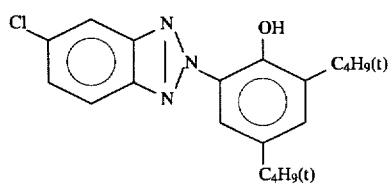 (i)
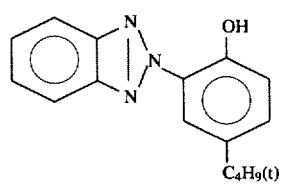 (ii)
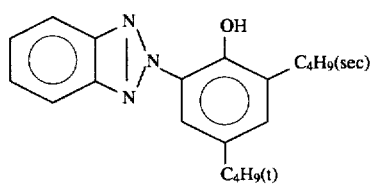 (iii)
Image-dye stabilizer (Cpd-7)
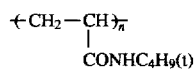
Average molecular weight: 60,000
Image-dye stabilizer (Cpd-8)
Mixture (1:1 in weight ratio) of
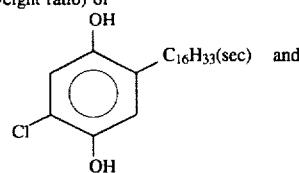 and 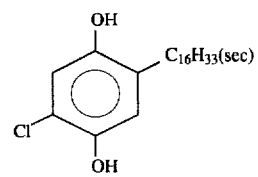
Image-dye stabilizer (Cpd-9)   Antiseptic (Cpd-10)
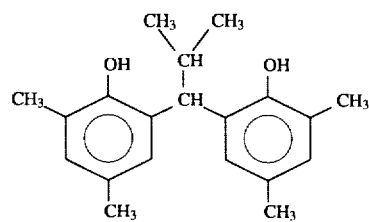 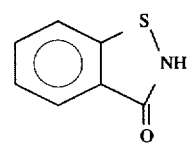
Antiseptic (Cpd-11)
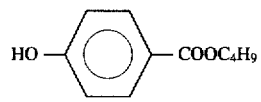

Ultraviolet-absorbing agent (UV-1)
Mixture ((iv):(v):(vi) = 4:2:4 in weight ratio) of (iv) 2-(2H-benzotriazol-2-yl)-4,6-di-tert-pentylphenol, with $C_5H_{11}(t)$ groups (v) 2-(5-chloro-2H-benzotriazol-2-yl)-4,6-di-tert-butylphenol, with $C_4H_9(t)$ groups (vi) 2-(2H-benzotriazol-2-yl)-4,6-di-sec-butylphenol, with $C_4H_9(sec)$ groups Solvent (Solv-1)

Dibutyl phthalate: benzene-1,2-di(COOC$_4$H$_9$)

Solvent (Solv-2)
Mixture (1:1 in weight ratio) of $O=P(O-C_6H_4-C_3H_7(iso))_3$ and $O=P(O-C_6H_4-CH_3)_3$ Solvent (Solv-3)

$O=P(O-C_9H_{19}(iso))_3$

Solvent (Solv-4)

$O=P(O-C_6H_4-CH_3)_3$

Solvent (Solv-5)

$\begin{array}{c} COOC_8H_{17} \\ | \\ (CH_2)_8 \\ | \\ COOC_8H_{17} \end{array}$ Solvent (Solv-6)
Mixture (80:20 in volume ratio) of benzene-1,2-di(COO—C$_6$H$_{11}$) and $C_8H_{17}CHCH(CH_2)_7COOC_8H_{17}$ (with epoxide O)

Solvent (Solv-7)

$C_8H_{17}\underset{\underset{O}{\diagdown\diagup}}{CH}CH(CH_2)_7COOC_8H_{17}$

The thus obtained multi-layer color photographic printing paper A was subjected to continuous processings (running tests). That is, the color photographic printing paper A was image-wise exposed to light and was continuously processed using an automatic printer FAP 3500 (manufactured by Fuji Photo Film Co., Ltd.) in the below described processing steps using solutions having the below described compositions, until the replenishing amount reached twice the volume of the color-developing tank. The composition of color developer was changed as shown in Table 1.

| Processing Step | Temperature (°C.) | Time (sec) | Replenisher (ml/m²) | Tank Volume (liter) |
|---|---|---|---|---|
| Color developing | 38.5 | 45 | 60 | 17 |
| Bleach-fixing | 30–35 | 45 | 60 | 17 |
| Rinse (1) | 30–35 | 20 | — | 8 |
| Rinse (2) | 30–35 | 20 | — | 8 |
| Rinse (3) | 30–35 | 20 | — | 8 |
| Rinse (4) | 30–35 | 30 | 200 | 8 |

Note: Rinsing steps were carried out in 4-tanks countercurrent mode from the tank of rinse (4) to (3) to (2) to (1).

The composition of each processing solution is as followed, respectively:

|  | Tank Solution | Replenisher |
|---|---|---|
| Color-developer |  |  |
| Water | 800 ml | 800 ml |
| Disodium ehylenediaminetetraacetate | 3 g | 3 g |
| Sodium catechol-3,5-disulfonate | 0.3 g | 0.3 g |
| Triethanolamine | 8.0 g | 8.0 g |
| Potassium bromide | 0.03 g | — |
| Sodium chloride | 6.0 g | — |
| N,N-di(sulfoethyl)hydroxylamine | 5.0 g | 8.0 g |
| Fluorescent whitening agent (WHITEX-4B, made by Sumitomo Chemical Ind.) | 1.0 g | 2.0 g |
| Sodium sulfite | 0.2 g | 0.2 g |
| Additive (See Table 1) | 0.02 g | 0.02 g |
| N-ethyl-N-(β-methanesulfonamidoethyl)-3-methyl-4-aminoaniline sulfate | 5.0 g | 12.0 g |
| Water to make | 1000 ml | 1000 ml |
| pH (25° C.) | 10.05 | 11.15 |
| Bleach-fixing solution (tank solution) |  |  |
| Water | 800 ml |  |
| Ammonium thiosulfate (50 wt %) | 120 ml |  |
| Ammonium sulfite | 17 g |  |
| Iron (III) ammonium ethylenediaminetetraacetate | 60 g |  |
| Disodium ethylenediaminetetraacetate | 3 g |  |
| Glacial acetic acid | 7 g |  |
| Water to make | 1000 ml |  |
| pH (25° C.) | 5.50 |  |
| Bleach-fixing solution (replenisher) |  |  |
| Water | 500 ml |  |
| Ammonium thiosulfate (50 wt %) | 220 ml |  |
| Ammonium sulfite | 35 g |  |
| Iron (III) ammonium ethylenediaminetetraacetate | 110 g |  |
| Disodium ethylenediaminetetraacetate | 3 g |  |
| Glacial acetic acid | 25 g |  |
| Water to make | 1000 ml |  |
| pH (25° C.) | 4.80 |  |
| Rinse solution (Both tank solution and replenisher) |  |  |
| Ion-exchanged water (calcium and magnesium each are 3 ppm or below) |  |  |

In each running test, at the start of the running and after the completion thereof, each sample was subjected to gradation exposure through a filter for sensitometry by using a sensitometer (manufactured by Fuji Photo Film Co., Ltd.; FWH model; the color temperature of the light source: 3200K) (at that time, the exposure was made such that the exposure amount is 250 CMS for an exposure time of 0.1 sec). The thus exposed sample was developed and the density of the developed sample was measured by an automatic recording densitometer, to obtain each photographic properties of magenta at the start and the end of processing.

The same running test as the above, except that the replenisher amount was lowered to 55 ml/m² with respect to each color developer, was carried out, and each photographic properties of magenta was determined, to obtain the decrement of sensitivity (log E value) from said photographic properties at both the start and the end of running test. Results are shown in Table 1.

Additives (A), (B), and (C) are the following compounds.

(A) 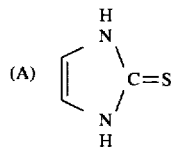

(B) H₃CHN—C—NHCH₃
       ‖
       S (C) Exemplified Compound in JP-A No. 238660/1989

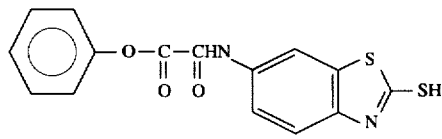

TABLE 1

| Color developer | | Change of magenta sensitivity (Δ logE) | | |
|---|---|---|---|---|
| No. | Compound added | At start | At end | Remarks |
| 1 | — | 0 | −0.14 | Comparison |
| 2 | (A) | −0.38 | −0.42 | " |
| 3 | (B) | −0.21 | −0.30 | " |
| 4 | (C) | −0.40 | −0.48 | " |
| 5 | I-1 | 0 | −0.01 | This invention |
| 6 | I-4 | 0 | −0.02 | " |
| 7 | I-7 | 0 | −0.02 | " |
| 8 | I-17 | 0 | −0.03 | " |
| 9 | I-19 | 0 | −0.03 | " |
| 10 | I-22 | 0 | −0.03 | " |

As is apparent from the results in Table 1, according to the present invention (Nos. 5 to 10), the addition of compound at the start does not affect to photographic properties, and the decrease of sensitivity does not occur despite of the amount of replenisher being lowered.

EXAMPLE 2

Multi-layer Color Photographic Printing Papers (B), (C), (D), (E), and (F) were prepared in the same manner as Multi-layer Color Photographic Printing Paper (A) of Example 1, except that the magenta coupler in Example 1 was respectively changed as shown in the following, in each equimolar amount:

| Sample | Magenta coupler |
|---|---|
| Photographic Printing Paper (A) | Same as in Example 1 |
| Photographic Printing Paper (B) | M-1 |
| Photographic Printing Paper (C) | M-2 |
| Photographic Printing Paper (D) | M-A |
| Photographic Printing Paper (E) | M-B |
| Photographic Printing Paper (F) | M-C |

Magenta couplers M-A, M-B, and M-C are as follows:

M-A

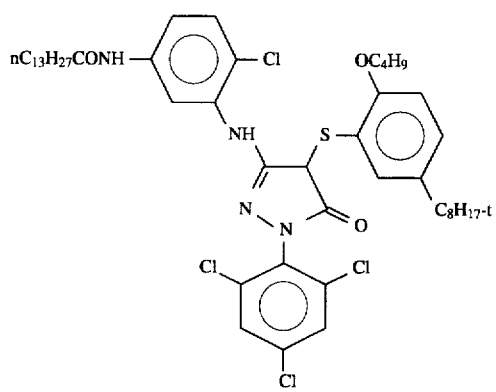

M-B

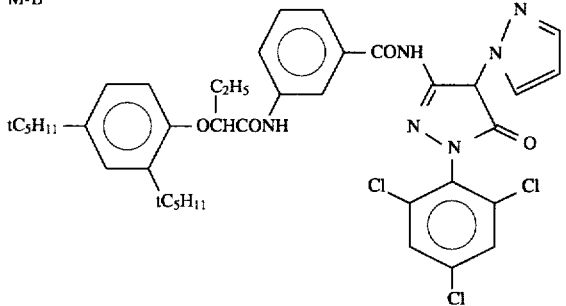

M-C

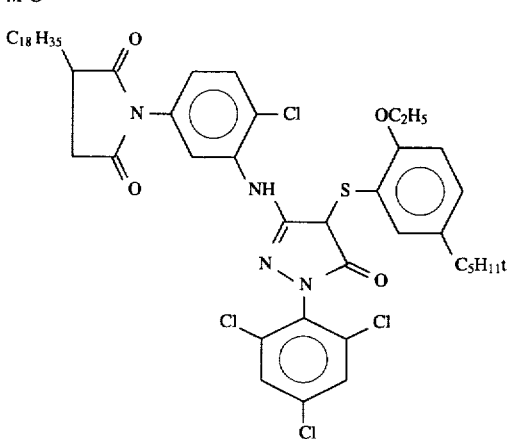

The thus obtained multi-layer color photographic printing papers were subjected to a running test in the same manner as in Example 1 using color developer No. 1, 2, 5, or 6, and, in the same manner as Example 1, the changes of sensitivity of magenta between the start and the end of running test were evaluated. The results are summarized in Table 2.

TABLE 2

| Test No. | Color developer | Color photographic printing paper | Change of magenta sensitivity ($\Delta$ logE) | | Remarks |
|---|---|---|---|---|---|
| | | | At start | At end | |
| 1 | No. 1 | A | 0 | −0.14 | Comparison |
| 2 | " | B | 0 | −0.15 | Comparison |
| 3 | " | C | 0 | −0.15 | Comparison |
| 4 | " | D | 0 | −0.11 | Comparison |
| 5 | " | E | 0 | −0.12 | Comparison |
| 6 | " | F | 0 | −0.12 | Comparison |
| 7 | No. 2 | A | −0.38 | −0.42 | Comparison |
| 8 | " | B | −0.40 | −0.44 | Comparison |
| 9 | " | C | −0.42 | −0.49 | Comparison |
| 10 | " | D | −0.28 | −0.30 | Comparison |
| 11 | " | E | −0.21 | −0.33 | Comparison |
| 12 | " | F | −0.23 | −0.31 | Comparison |
| 13 | No. 5 | A | 0 | −0.01 | This invention |
| 14 | " | B | 0 | −0.01 | This invention |
| 15 | " | C | 0 | −0.01 | This invention |
| 16 | " | D | 0 | −0.05 | This invention |
| 17 | " | E | 0 | −0.05 | This invention |
| 18 | " | F | 0 | −0.04 | This invention |
| 19 | No. 6 | A | 0 | −0.02 | This invention |
| 20 | " | B | 0 | −0.02 | This invention |
| 21 | " | C | 0 | −0.02 | This invention |
| 22 | " | D | 0 | −0.05 | This invention |
| 23 | " | E | 0 | −0.06 | This invention |
| 24 | " | F | 0 | −0.06 | This invention |

As is apparent from the results in Table 2, according to the present invention, the change of the photographic properties due to the addition of compound at the start does not occur at all, and the decrease of sensitivity does occur scarcely despite of the amount of replenisher being lowered. In particular, the effect is remarkable when a magenta coupler represented by formula (M) is used (Test Nos. 13, 14, 15, 19, 20, and 21).

EXAMPLE 3

After the surface of a paper support, whose both surfaces were laminated with polyethylene, was subjected to corona discharge treatment, a gelatin undercoat layer containing sodium dodecylbenzenesulfonate was provided thereon, and various photographic constitutional layers were applied, to prepare a multi-layer color photographic printing paper (301) having the below-given layer constitution. The coating solution were prepared as follows:

Preparation Of the First Layer Coating Solution 153.0 Grams of yellow coupler (ExY), 15.0 g of image-dye stabilizer (Cpd-1), 7.5 g of image-dye stabilizer (Cpd- 2), and 16.0 g of image-dye stabilizer (Cpd-3) were dissolved in 25 g of solvent (Solv-1), 25 g of solvent (Solv-2 and 180 ml of ethyl acetate, and the solution was added into 1,000 g of 10% aqueous gelatin solution containing 60 ml of 10% sodium dodecylbenzene-sulfonate and 10 g of citric acid, and emulsified and dispersed, to prepare an emulsified dispersion A. Separately, a silver chlorobromide emulsion A (comprising cubic silver halide grains made up of a mixture of a large size emulsion A having an average grain size of 0.88 μm and a small size A emulsion having an average grain size of 0.70 μm in a molar ratio of 3:7 in terms of silver, wherein the deviation coefficients of the grain size distributions are 0.08 and 0.10, respectively; each of the emulsions has 0.3 mol % of silver bromide being localized on the surface of the grains; and the remaining part of grain is made of silver chloride) was prepared. In this emulsion, blue-sensitive sensitizing dyes A and B, shown below, respectively were added in such amounts of $2.0 \times 10^{-4}$ mol to the large size emulsion A and $2.5 \times 10^{-4}$ mol to the small size emulsion A, per mol of silver. The chemical ripening of this emulsion was carried out by adding a sulfur sensitizing agent and a gold sensitizing agent. The above-described emulsified dispersion A and this silver chlorobromide emulsion A were mixed together and dissolved to give the composition shown below, thereby preparing the first layer coating solution.

Coating solutions for the second to seventh layers were prepared in the same manner as the first layer coating solution. As the gelatin hardener of each layer, 1-hydroxy-3,5-dichloro-s-triazine sodium salt was used.

Further, Cpd-14 and Cpd-15, shown below, were added to each layer so that the total amounts thereof might be 25.0 mg/m$^2$ and 50.0 mg/m$^2$, respectively.

In the silver chlorobromide emulsions of photosensitive emulsion layers, the following spectral sensitizing dyes were used.

Blue-sensitive emulsion layer:

Sensitizing dye A

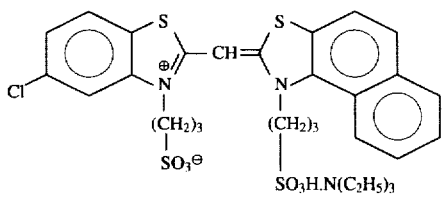

and

Sensitizing dye B

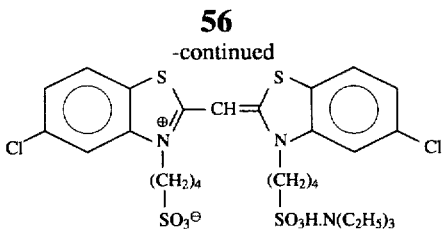

(each $2.0 \times 10^{-4}$ mol to the large size emulsion and $2.5 \times 10^{-4}$ mol to the small size emulsion, per mol of silver halide.)

Green-sensitive emulsion layer:

Sensitizing dye C

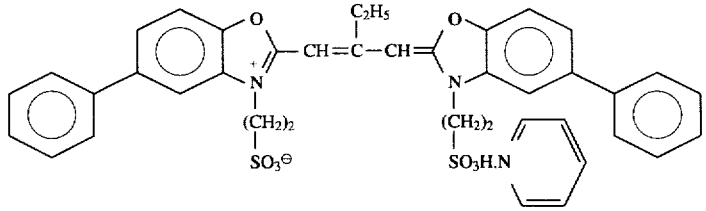

($4.0 \times 10^{-4}$ mol to the large size emulsion and $5.6 \times 10^{-4}$ mol to the small size emulsion, per mol of silver halide) and Sensitizing dye D

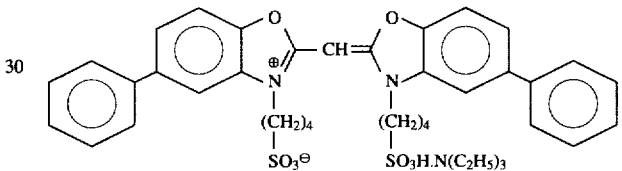

($7.0 \times 10^{-5}$ mol to the large size emulsion and $1.0 \times 10^{-5}$ mol to the small size emulsion, per mol of silver halide)

Red-sensitive emulsion layer:

Sensitizing dye E

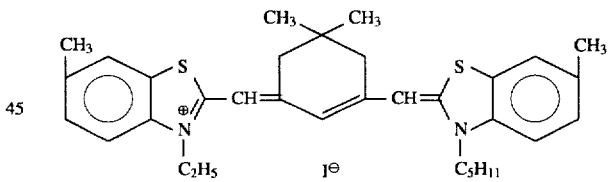

($0.9 \times 10^{-4}$ mol to the large size emulsion and $1.1 \times 10^{-4}$ mol to the small size emulsion, per mol of silver halide)

To the red-sensitive emulsion layer, the following compound was added in an amount of $2.6 \times 10^{-3}$ mol per mol of silver halide:

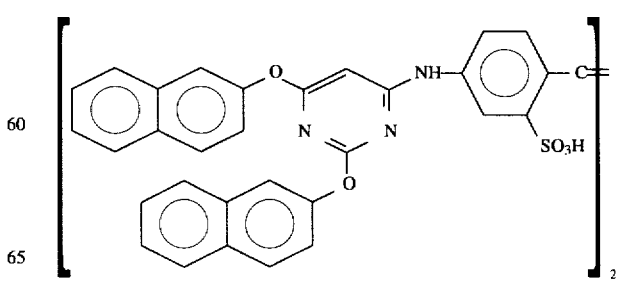

Further, respectively to the blue-sensitive emulsion layer, the green-sensitive emulsion layer, and the red-sensitive emulsion layer, was added 1-(5-methylureidophenyl)-5-mercaptotetrazole in respective amounts of $8.5 \times 10^{-5}$ mol, $7.7 \times 10^{-4}$ mol, and $2.5 \times 10^{-4}$ mol, per mol of the silver halide.

Further, respectively to the blue-sensitive emulsion layer and the green-sensitive emulsion layer, was added 4-hydroxy-6-methyl-1,3,3a,7-tetrazaindene in respective amounts of $1 \times 10^{-4}$ mol and $2 \times 10^{-4}$ mol, per mol of the silver halide.

Further, to prevent irradiation, the following dye (the coating amount is indicated in parentheses) was added to the emulsion layers.

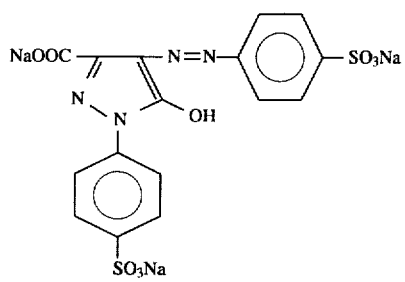 (10 mg/m²)

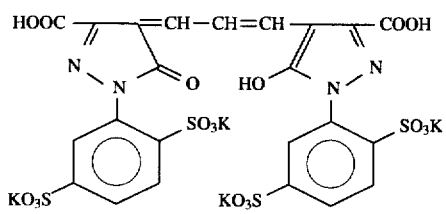 (10 mg/m²)

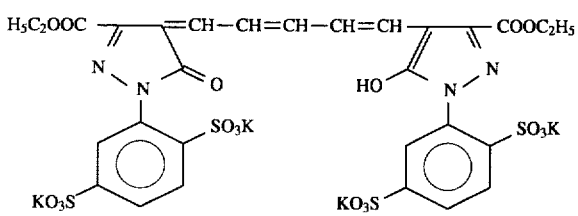 (40 mg/m²)

and

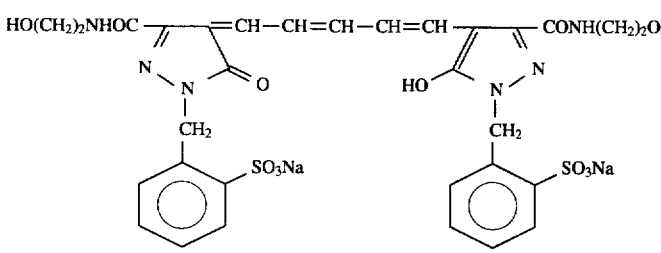 (20 mg/m²)

(Layer Composition)

The layer compositions of the layers are shown below. The numerals indicate coating amounts (g/m²). The coating amount of each of the silver halide emulsions is in terms of silver.

Support

Paper laminated on both sides with polyethylene (a white pigment, $TiO_2$, and a bluish dye, ultramarine, were included in the first layer side of the polyethylene-laminated film)

First Layer (Blue-sensitive emulsion layer)

| | |
|---|---|
| The above-described silver chlorobromide emulsion A | 0.27 |
| Gelatin | 1.36 |
| Yellow coupler (ExY) | 0.79 |
| Image-dye stabilizer (Cpd-1) | 0.08 |
| Image-dye stabilizer (Cpd-2) | 0.04 |
| Image-dye stabilizer (Cpd-3) | 0.08 |
| Solvent (Solv-1) | 0.13 |
| Solvent (Solv-2) | 0.13 |

Second Layer (Color-mix preventing layer)

| | |
|---|---|
| Gelatin | 1.00 |
| Color mix inhibitor (Cpd-4) | 0.06 |
| Solvent (Solv-7) | 0.03 |
| Solvent (Solv-2) | 0.25 |
| Solvent (Solv-3) | 0.25 |

Third Layer (Green-sensitive emulsion layer)

Silver chlorobromide emulsion (comprising cubic silver halide grains made up of a mixture of a large size emulsion B having an average grain size of 0.55 μm and a small size emulsion B having an average grain size of 0.39 μm in a molar ratio of 1:3 in terms of silver, wherein the deviation coefficients of the grain size distributions are 0.10 and 0.08 respectively; each of the emulsions has 0.8 mol % of AgBr being localized on the surface of the grains; and the remaining part of grain is AgCl) 0.13

| | |
|---|---|
| Gelatin | 1.45 |
| Magenta coupler (ExM) | 0.16 |
| Image-dye stabilizer (Cpd-5) | 0.15 |
| Image-dye stabilizer (Cpd-2) | 0.03 |
| Image-dye stabilizer (Cpd-6) | 0.01 |
| Image-dye stabilizer (Cpd-7) | 0.01 |
| Image-dye stabilizer (Cpd-8) | 0.08 |
| Solvent (Soly-3) | 0.50 |
| Solvent (Solv-4) | 0.15 |
| Solvent (Solv-5) | 0.15 |

Fourth Layer (Color-mix preventing layer)

| | |
|---|---|
| Gelatin | 0.70 |
| Color-mix inhibitor (Cpd-4) | 0.04 |
| Solvent (Solv-7) | 0.02 |
| Solvent (Solv-2) | 0.18 |
| Solvent (Solv-3) | 0.18 |

Fifth Layer (Red-sensitive emulsion layer)

Silver chlorobromide emulsion (comprising cubic silver halide grains made up of a mixture of a large size emulsion C having an average grain size of 0.50 μm and a small size emulsion C having an average grain size of 0.41 μm in a molar ratio of 1:4 in terms of silver, wherein the deviation coefficients of the grain size distributions are 0.09 and 0.11 respectively; each of the emulsions has 0.8 mol % of AgBr being localized on the surface of the grains; and the remaining part of grain is AgCl) 0.20

| | |
|---|---|
| Gelatin | 0.85 |
| Cyan coupler (ExC) | 0.33 |
| Ultraviolet-absorbing agent (UV-2) | 0.18 |
| Image-dye stabilizer (Cpd-9) | 0.15 |
| Image-dye stabilizer (Cpd-10) | 0.15 |
| Image-dye stabilizer (Cpd-11) | 0.01 |
| Solvent (Solv-6) | 0.22 |
| Image-dye stabilizer (Cpd-8) | 0.01 |
| Image-dye stabilizer (Cpd-6) | 0.01 |
| Solvent (Solv-1) | 0.01 |
| Image-dye stabilizer (Cpd-1) | 0.33 |

Sixth layer (Ultraviolet-absorbing layer)

| | |
|---|---|
| Gelatin | 0.55 |
| Ultraviolet-absorbing agent (UV-1) | 0.38 |
| Image-dye stabilizer (Cpd-12) | 0.15 |
| Image-dye stabilizer (Cpd-5) | 0.02 |

Seventh layer (Protective layer)

| | |
|---|---|
| Gelatin | 1.13 |
| Acryl-modified copolymer of polyvinyl alcohol (modification degree: 17%) | 0.05 |
| Liquid paraffin | 0.02 |
| Image-dye stabilizer (Cpd-13) | 0.01 |

Compounds used are as follows:

Yellow coupler (ExY)
Mixture (1:1 in molar ratio) of (a) and (b)

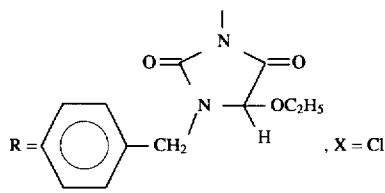 (a)

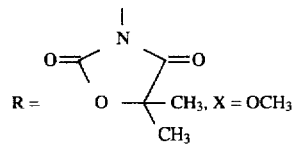 (b)

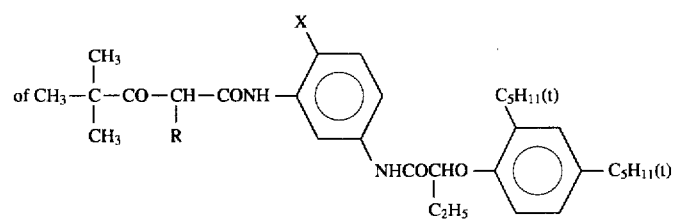

Magenta coupler (ExM)
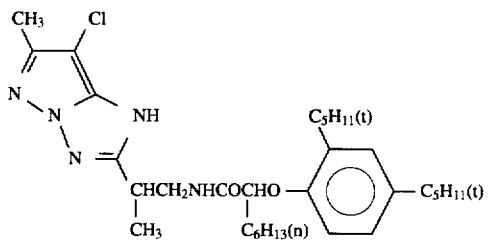
Cyan coupler (ExC)
Mixture (1:1 in molar ratio) of
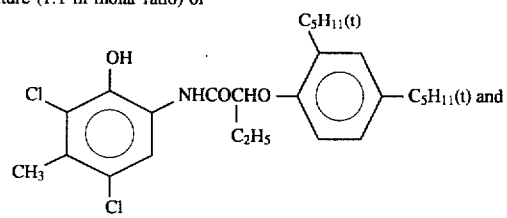 and 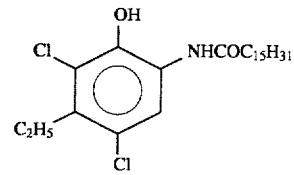
Image-dye stabilizer (Cpd-1)
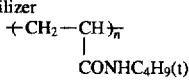
Average molecular weight: 60,000
Image-dye stabilizer (Cpd-2)
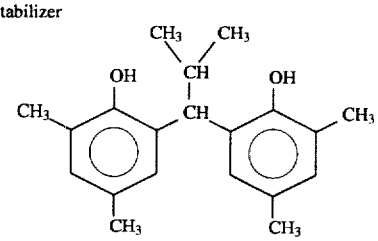
Image-dye stabilizer (Cpd-3)
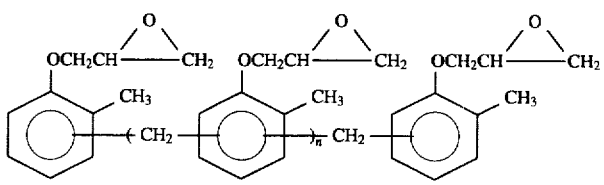
n = 7 to 8 (average)
Color-mix inhibitor (Cpd-4)
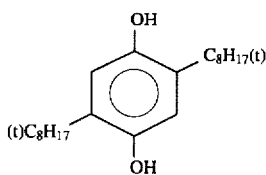
Image-dye stabilizer (Cpd-5)
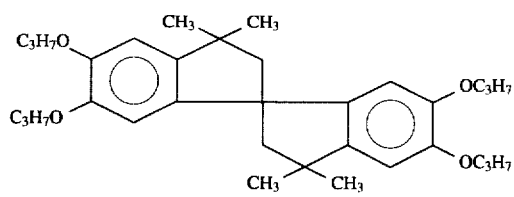
Image-dye stabilizer (Cpd-6)
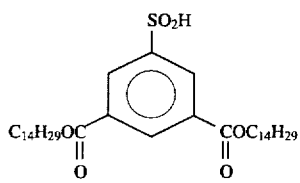
Image-dye stabilizer (Cpd-7)

Image-dye stabilizer (Cpd-8)

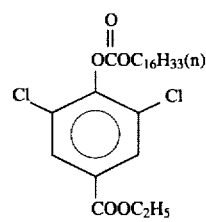

Image-dye stabilizer (Cpd-9)

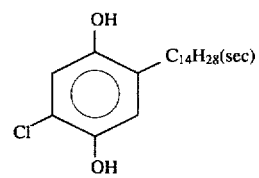

Image-dye stabilizer (Cpd-10)

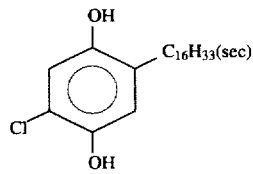

Image-dye stabilizer (Cpd-11)

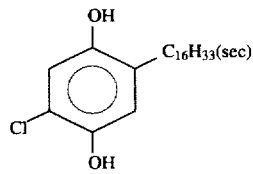

Image-dye stabilizer (Cpd-12)

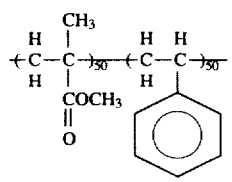

Image-dye stabilizer (Cpd-13)

$$C_{13}H_{27}CONH(CH_2)_3\overset{\underset{\displaystyle CH_3}{|}}{\underset{\underset{\displaystyle CH_3}{|}}{N^{\oplus}}}CH_2COO^{\ominus}$$

Average molecular weight: 60,000

Antiseptic (Cpd-14)

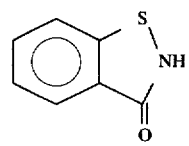

Antiseptic (Cpd-15)

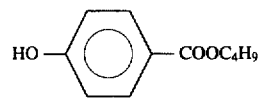

Ultraviolet-absorbing agent (UV-1)
Mixture ((i):(ii):(iii):(iv) = 10:5:1:5 in weight ratio) of

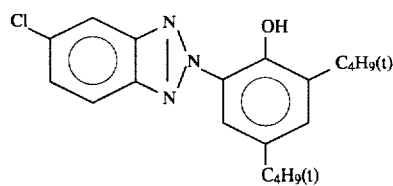 (i)

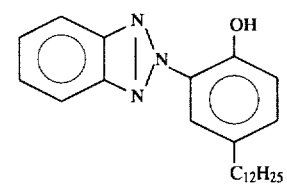 (ii)

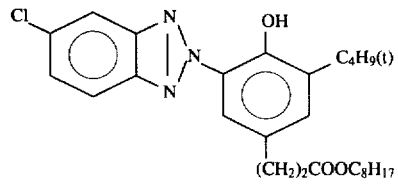 (iii)

(iv)

Ultraviolet-absorbing agent (UV-2)
Mixture of ((v):(vi):(vii) = 1:2:2 in weight ratio) of

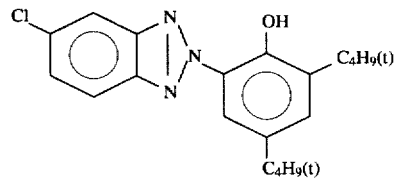 (v)

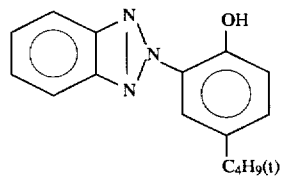 (vi)

Solvent 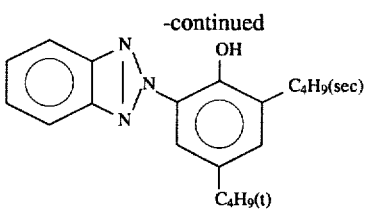 (vii)

Solvent (Solv-1)    Solvent 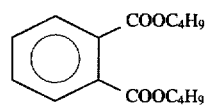 (Solv-2)

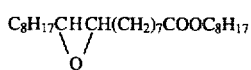

Solvent (Solv-3)    Solvent (Solv-4)

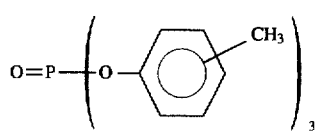    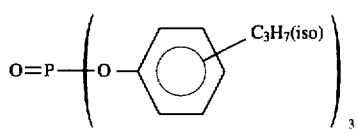

Solvent (Solv-5)    Solvent (Solv-6)

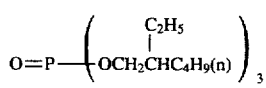    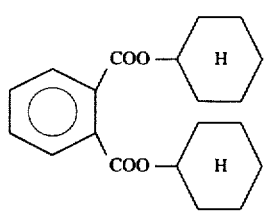

Solvent (Solv-7)

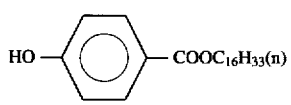

The thus obtained multi-layer color photographic printing paper 301 was image-wise exposed to light and was continuously processed (running test) in the below described processing steps using solutions having the below described compositions, until the replenishing amount reached twice the volume of the color-developing tank, in the same manner as Example 1, except that the composition of developer was changed as shown in Table 3.

| Processing Step | Temperature (°C.) | Time (sec) | Replenisher (ml/m²) | Tank Volume (liter) |
|---|---|---|---|---|
| Color developing | 38 | 30 | 100 | 10 |
| Bleach-fixing | 30–35 | 30 | 60 | 10 |
| Rinse (1) | 30–35 | 20 | — | 7 |
| Rinse (2) | 30–35 | 20 | — | 7 |
| Rinse (3) | 30–35 | 20 | 200 | 7 |

Note: Rinsing steps were carried out in 3-tanks countercurrent mode from the tank of rinse (3) → (2) → (1).

The composition of each processing solution is as followed, respectively:

| | Tank Solution | Replenisher |
|---|---|---|
| Color-developer | | |
| Water | 800 ml | 800 ml |
| Diehylenetriaminepentaacetic acid | 3 g | 3 g |
| Sodium catechol-3,5-disulfonate | 0.3 g | 0.3 g |
| Triethanolamine | 8.0 g | 8.0 g |
| Potassium bromide | 0.02 g | — |
| Sodium chloride | 4.0 g | — |
| N,N-di(sulfoethyl)hydroxylamine | 5.0 g | 7.0 g |
| Fluorescent whitening agent (UVITEX CK, made by Ciba Geigy) | 1.0 g | 1.5 g |
| Sodium sulfite | 0.1 g | 0.1 g |
| Additive (See Table 1) | 0.1 g | 0.1 g |
| N-ethyl-N-(β-methane-sulfonamidoethyl)-3-methyl-4-aminoaniline sulfate | 5.0 g | 10.0 g |
| Water to make | 1000 ml | 1000 ml |
| pH (25° C.) | 10.05 | 11.00 |
| Bleach-fixing solution (tank solution) | | |
| Water | 800 ml | |
| Ammonium thiosulfate (50 wt %) | 120 ml | |
| Ammonium sulfite | 17 g | |
| Iron (III) ammonium ethylenediamine-tetraacetate | 60 g | |

-continued

|  | Tank Solution | Replenisher |
|---|---|---|
| Disodium ethylenediaminetetraacetate | 3 g | |
| Glacial acetic acid | 7 g | |
| Water to make | 1000 ml | |
| pH (25° C.) | 5.50 | |
| Bleach-fixing solution (replenisher) | | |
| Water | 500 ml | |
| Ammonium thiosulfate (50 wt %) | 240 ml | |
| Ammonium sulfite | 35 g | |
| Iron (III) ammonium ethylenediamine-tetraacetate | 130 g | |
| Disodium ethylenediaminetetraacetate | 3 g | |
| Glacial acetic acid | 25 g | |
| Water to make | 1000 ml | |
| pH (25° C.) | 4.80 | |
| Rinse solution (Both tank solution and replenisher) | | |
| Ion-exchanged water (calcium and magnesium each are 3 ppm or below) | | |

In each running test, 0.4 ml/l of bleach-fix solution ($2.8 \times 10^{-4}$ mol/l as thiosulfate) was added to each color developer of processing solutions, and the change of sensitivity of magenta (Δlog E) and the change of maximum density of magenta (ΔDmax) before and after the addition of thosulfate was determined. Results are shown in Table 3. (Additives A, B, and C were the same as in Example 1).

TABLE 3

| Test No. | Additive | Change of photographic properties | | Remarks |
|---|---|---|---|---|
| | | Δ logE | Δ Dmax | |
| 1 | — | −0.18 | −0.29 | Comparison |
| 2 | (A) | −0.20 | −0.33 | " |
| 3 | (B) | −0.23 | −0.38 | " |
| 4 | (C) | −0.24 | −0.40 | " |
| 5 | I-1 | −0.02 | −0.03 | This invention |
| 6 | I-4 | −0.03 | −0.06 | " |
| 7 | I-14 | −0.03 | −0.06 | " |
| 8 | I-15 | −0.04 | −0.06 | " |
| 9 | I-19 | −0.04 | −0.06 | " |
| 10 | I-23 | −0.03 | −0.05 | " |

As is apparent from the results in Table 3, according to the present invention, the change of the photographic properties is lowered remarkably despite of the contamination of color developer by bleach-fix solution.

EXAMPLE 4

When magenta couplers M-10, M-16, M-18, M-26, M-35, and M-38 each are used instead of magenta coupler M-1 in Example 1, the fluctuation of sensitivity is restrained by using a thiourea compound in the same manner as Example 1.

Having described our invention as related to the present embodiments, it is our intention that the invention not be limited by any of the details of the description, unless otherwise specified, but rather be construed broadly within its spirit and scope as set out in the accompanying claims.

What we claim is:

1. A method for processing a silver halide color photographic material, which comprises processing said silver halide color photographic material containing at least one pyrazoloazole magenta coupler represented by formula (M) with a color developer comprising at least one thiourea compound represented by formula (I) and at least one p-phenylenediamine derivative as a color developing agent:

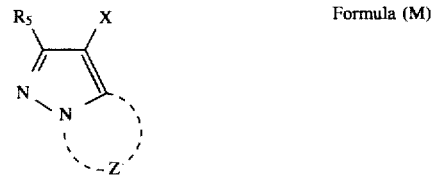

Formula (M)

wherein $R_5$ represents a hydrogen atom or a substituent, Z represents a group of non-metallic atoms required to form a 5-membered azole ring containing 2 to 4 nitrogen atoms, which azole ring may contain a substituent, and X represents a group capable of being released upon coupling reaction with the oxidized product of a developing agent,

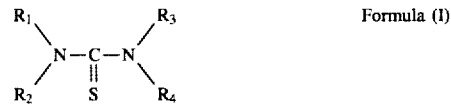

Formula (I)

wherein $R_1$, $R_2$, $R_3$, and $R_4$ each represent a hydrogen atom, a substituted or unsubstituted alkyl group, a substituted or unsubstituted aryl group, or a substituted or unsubstituted cycloalkylene group, provided that two or more of $R_1$, $R_2$, $R_3$, and $R_4$ each do not represent a hydrogen atom at the same time; at least one pair of $R_1$ and $R_3$, and $R_2$ and $R_4$, together may bond to form a nitrogen-containing heterocyclic ring; or at least one pair of $R_1$ and $R_2$, and $R_3$ and $R_4$, together may bond to form a ring.

2. The method for processing a silver halide color photographic material as claimed in claim 1, wherein the alkyl group represented by $R_1$, $R_2$, $R_3$, or $R_4$ in formula (I) is an alkyl group having about 1 to 10 carbon atoms.

3. The method for processing a silver halide color photographic material as claimed in claim 1, wherein the aryl group represented by $R_1$, $R_2$, $R_3$, or $R_4$ in formula (I) is a phenyl group or a napthalene group.

4. The method for processing a silver halide color photographic material as claimed in claim 1, wherein the cycloalkyl group represented by $R_1$, $R_2$, $R_3$, or $R_4$ in formula (I) is a cyclopropane group or a cyclohexyl group.

5. The method for processing a silver halide color photographic material as claimed in claim 1, wherein at least one pair of $R_1$ and $R_3$, and $R_2$ and $R_4$, in formula (I), together bonds to form a 5- or 6-membered nitrogen-containing heterocyclic ring.

6. The method for processing a silver halide color photographic material as claimed in claim 1, wherein at least one pair of $R_1$ and $R_2$, and $R_3$ and $R_4$, in formula (I), together bonds to form a 6-membered aliphatic, aromatic or heterocyclic ring.

7. The method for processing a silver halide color photographic material as claimed in claim 1, wherein the amount of thiourea compound represented by formula (I) to be added is 0.001 to 10 g per liter of said color developer.

8. The method for processing a silver halide color photographic material as claimed in claim 1, wherein said color developer is substantially free from benzyl alcohol.

9. The method for processing a silver halide color photographic material as claimed in claim 1, wherein said color developer is substantially free from sulfite ions.

10. The method for processing a silver halide color photographic material as claimed in claim 1, wherein the skeleton of coupler represented by formula (M) is selected from the group consisting of 1H-imidazo-[1,2-b]pyrazole, 1H-pyrazolo[1,5-b][1,2,4]triazole, 1H-pyrazolo[5,1-c][1,2,4]triazole, 1H-pyrazolo[1,5-d]tetrazole, and 1H-pyrazolo[1,5-a]benzimidazole.

11. The method for processing a silver halide color photographic material as claimed in claim 1, wherein the amount of pyrazoloazole magenta coupler contained in said silver halide color photographic material is 0.02 to 2.0 mol per mol of silver halide.

12. The method for processing a silver halide color photographic material as claimed in claim 1, wherein said color developer contains thiosulfate radicals in an amount of $2\times10^{-4}$ to $1\times10^{-1}$ mol/l.

13. The method for processing a silver halide color photographic material as claimed in claim 1, wherein the processing temperature by said color developer is 20° to 50° C.

14. The method for processing a silver halide color photographic material as claimed in claim 1, wherein the processing time by said color developer is 20 sec to 5 min.

15. The method for processing a silver halide color photographic material as claimed in claim 1, wherein the replenishing amount of color developer is 20 to 600 ml per $m^2$ of said silver halide color photographic material.

16. The method for processing a silver halide color photographic material as claimed in claim 1, wherein the photographic material is subjected to a bleaching process or a bleach-fixing process after color development.

17. The method for processing a silver halide color photographic material as claimed in claim 1, wherein the photographic material is subjected to a bleach-fixing process after color development.

18. The method for processing a silver halide color photographic material as claimed in claim 1, wherein the processing is conducted by a continuous and automatic process.

19. The method for processing a silver halide color photographic material as claimed in claim 1, wherein the replenishing amount of the color developer is 40 to 100 ml per $m^2$ of said silver halide color photographic material.

20. A method for processing a silver halide color photographic material, which comprises processing silver halide color photographic material containing 0.02 to 2.0 mol of at least one pyrazoloazole magenta coupler represented by formula (M) per mol of silver halide with a color developer comprising 0.001 to 10 g of at least one thiourea compound per liter of color developer, represented by formula (I) and about 0.1 g to about 20 g of at least one p-phenylenediamine derivative as a color developing agent per liter of color developer:

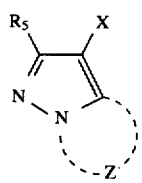

Formula (M)

wherein $R_5$ represents a hydrogen atom or a substituent, Z represents a group of non-metallic atoms required to form a 5-membered azole ring containing 2 to 4 nitrogen atoms, which azole ring may contain a substituent, and X represents a group capable of being released upon coupling reaction with the oxidized product of a developing agent,

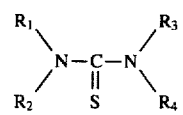

Formula (I)

wherein $R_1$, $R_2$, $R_3$, and $R_4$ each represent a hydrogen atom, a substituted or unsubstituted alkyl group, a substituted or unsubstituted aryl group, or a substituted or unsubstituted cycloalkylene group, provided that two or more of $R_1$, $R_2$, $R_3$, and $R_4$ each do not represent a hydrogen atom at the same time; at least one pair of $R_1$ and $R_3$, and $R_2$ and $R_4$, together may bond to form a nitrogen-containing heterocyclic ring, or at least one pair of $R_1$ and $R_2$, and $R_3$ and $R_4$, together may bond to form a ring.

21. A method for processing a silver halide color photographic material, which comprises processing in a continuous or automatic process said silver halide color photographic material containing 0.02 to 2.0 mol of at least one pyrazoloazole magenta coupler represented by formula (M) per mol of silver halide with a color developer comprising 0.05 to 1.0 g of at least one thiourea compound per liter of color developer, represented by formula (I) and about 0.5 g to about 10 g of at least one p-phenylenediamine derivative as a color developing agent per liter of color developer, wherein the amount of replenishment of said color developer is 40 to 100 ml per $M^2$ of said photographic material:

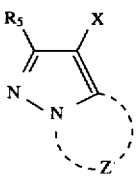

Formula (M)

wherein $R_5$ represents a hydrogen atom or a substituent, Z represents a group of non-metallic atoms required to form a 5-membered azole ring containing 2 to 4 nitrogen atoms, which azole ring may contain a substituent, and X represents a group capable of being released upon coupling reaction with the oxidized product of a developing agent,

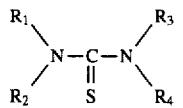

Formula (I)

wherein $R_1$, $R_2$, $R_3$, and $R_4$ each represent a hydrogen atom, a substituted or unsubstituted alkyl group, a substituted or unsubstituted aryl group, or a substituted or unsubstituted cycloalkylene group, provided that two or more of $R_1$, $R_2$, $R_3$, and $R_4$ each do not represent a hydrogen atom at the same time; at least one pair of $R_1$ and $R_3$, and $R_2$ and $R_4$, together may bond to form a monocyclic and/or 5- 6 membered ring.

22. A method for processing a silver halide color photographic material, which comprises processing said silver halide color photographic material containing 0.02 to 2.0 mol of at least one pyrazoloazole magenta coupler represented by formula (M) per mol of silver halide with a color developer comprising 0.05 to 1.0 g of at least one thiourea compound per liter of color developer, represented by formula (I) and about 0.1 g to about 20 g of at least one p-phenylenediamine derivative as a color developing agent per liter of color developer, wherein the color developer solution is substantially free from benzyl alcohol and/or substantially free from sulfite ions:

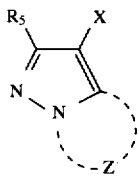

Formula (M)

wherein $R_5$ represents a hydrogen atom or a substituent, Z represents a group of non-metallic atoms required to form a 5-membered azole ring containing 2 to 4 nitrogen atoms, which azole ring may contain a substituent, and X represents a group capable of being released upon coupling reaction with the oxidized product of a developing agent,

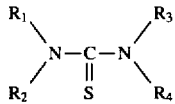

Formula (I)

wherein $R_1$, $R_2$, $R_3$, and $R_4$ each represent a hydrogen atom, a substituted or unsubstituted alkyl group, a substituted or unsubstituted aryl group, or a substituted or unsubstituted cycloalkylene group, provided that two or more of $R_1$, $R_2$, $R_3$, and $R_4$ each do not represent a hydrogen atom at the same time; at least one pair of $R_1$ and $R_3$, and $R_2$ and $R_4$, together may bond to form a monocyclic and/or 5-6 membered ring.

23. A method for processing a silver halide color photographic material, which comprises processing said silver halide color photographic material containing at least one pyrazoloazole magenta coupler represented by formula (M) with a color developer comprising at least one thiourea compound represented by formula (I) and at least one p-phenylenediamine derivative as a color developing agent:

Formula (M)

wherein $R_5$ represents a hydrogen atom or a substituent, Z represents a group of non-metallic atoms required to form a 5-membered azole ring containing 2 to 4 nitrogen atoms, which azole ring may contain a substituent, and X represents a group capable of being released upon coupling reaction with the oxidized product of a developing agent,

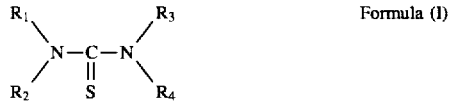

Formula (I)

wherein $R_1$, $R_2$, $R_3$, and $R_4$ each represent a hydrogen atom, a substituted or unsubstituted alkyl group, a substituted or unsubstituted aryl group, or a substituted or unsubstituted cycloalkylene group, provided that two or more of $R_1$, $R_2$, $R_3$, and $R_4$ each do not represent a hydrogen atom at the same time; or at least one pair of $R_1$ and $R_3$, and $R_2$ and $R_4$, together may bond to form a ring.

* * * * *